US007759057B2

(12) United States Patent
Zhou et al.

(10) Patent No.: US 7,759,057 B2
(45) Date of Patent: Jul. 20, 2010

(54) METHOD FOR ANALYZING MICROBIAL COMMUNITIES

(75) Inventors: Jizhong Zhou, Oak Ridge, TN (US); Liyou Wu, Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 564 days.

(21) Appl. No.: 10/943,067

(22) Filed: Sep. 16, 2004

(65) Prior Publication Data

US 2005/0282176 A1  Dec. 22, 2005

Related U.S. Application Data

(60) Provisional application No. 60/541,620, filed on Feb. 4, 2004.

(51) Int. Cl.
*C12Q 1/68* (2006.01)
(52) U.S. Cl. ......................................................... 435/6
(58) Field of Classification Search ........................ None
See application file for complete search history.

(56) References Cited

U.S. PATENT DOCUMENTS

| | | | |
|---|---|---|---|
| 5,536,871 A | 7/1996 | Nuovo et al. | |
| 5,605,824 A | 2/1997 | Nielson et al. | |
| 5,965,361 A | 10/1999 | Kigawa et al. | |
| 6,335,164 B1 * | 1/2002 | Kigawa et al. | ................. 435/6 |
| 6,541,277 B1 | 4/2003 | Kang et al. | |

FOREIGN PATENT DOCUMENTS

WO        WO 0043540 A1 *  7/2000

OTHER PUBLICATIONS

Lage et al. ("Whole genome analysis of genetic alterations in small DNA samples using hyperbranched strand displacement amplification and array-CGH" Genome Res. Feb. 2003;13(2):294-307).*
Detter et al. ("Isothermal strand-displacement amplification applications for high-throughput genomics" Genomics. Dec. 2002;80(6):691-8).*
Murray et al. ("DNA/DNA hybridization to microarrays reveals gene-specific differences between closely related microbial genomes" Proc Natl Acad Sci U S A. Aug. 14, 2001;98(17):9853-8).*
Wang et al. ("Large-scale identification, mapping, and genotyping of single-nucleotide polymorphisms in the human genome" Science. May 15, 1998;280(5366):1077-82).*
Dean FB, Hosono S, Fang LH, Wu XH, Faruqi AF, Bray-Ward P, Sun ZY, Zong QL, Du YF, Du J, Driscoll M, Song WM, Kingsmore SF, Egholm M, Lasken RS; Comprehensive human genome amplification using multiple displacement amplification. Proc Natl Acad Sci 2002, 99:5261-5266.
DeRisi JL, Iyer VR, Brown PO. Exploring the metabolic and genetic control of gene expression on a genomic scale. Science 1997, 278:680-686.
Lage JM, Leamon JH, Pejovic T, Hamann S, Lacey M, Dillon D, Segraves R, Vossbrinck B, Gonzalez A, Pinkel D, Albertson DG, Costa J, Lizardi PM. Whole genome analysis of genetic alterations in small DNA samples using hyperbranched strand displacement amplification and array-CGH. Genome Research 2003, 13: 294-307.
Liu Y, Zhou J, Omelchenko M, Bellaev A, Venkateswaran A, Stair J, Wu L, Thompson DK, Xu D, Rogozin IB et al. Transcriptome dynamics of Deinococcus radiodurans recovering from ionizing radiation. Proc Natl Acad Scl USA 2003, 100: 4191-4196.
Loy A, Lahner A, Lee N, Adamczyk J, Meier H, Ernst J, Schleifer KH, Wagner M. Oligonucleotide microarray for 16S rRNA gene-based detection of all recognized lineages of sulfate-reducing prokaryotes in the environment. Appl Environ Microbiol, 2002, 68:5064-5081.
Nallur GC, Luo H, Fang LH, Cooley S, Dave V, Lambert J, Kukanskis K, Kingsmore S, Lasken R, Schweitzer B. Signal amplification by rolling circle amplification on DNA microarrays. Nucleic Acid Res 2001, 29:E118.
Rhee, S.K., Liu, X.D., Wu, L.Y., Chong, S.C., Wan, X.F., and Zhou, J.Z. Detection of genes Involved in biodegradation and biotransformation in microbial communities by using 50-mer oligonucleotide microarrays. Applied and Environmental Microbiology 2004, 70: 4303-4317.
Taroncher-Oldenburg G, Griner EM, Francis CA, Ward BB. Oligonucleotide microarray for the study of functional gene diversity in the nitrogen cycle in the environment. Appl Environ Microbiol 2003, 69:1159-1171.
Tiquia SM., Wu LY, Chong SC, Passovets S, Xu D, Xu Y, and Zhou JZ. Evaluation of 50-mer oligonucleotide arrays for detecting microbial populations in environmental samples. BiotechnIques 2004, 36: 664-675.
Wu HC, Shieh J, Wright DJ, Azarani A. DNA sequencing using rolling circle amplication and precision glass syringes in a high-throughput liquid handling system. Biotechniques 2003a, 34:204-207.
Wu LY, Thompson DK, Xueduan L, Bagwell CE, et al. Development and evaluation of microarray-based whole-genome hybridization for detection of microorganisms within the context of environmental applications. Environmental Science and Technology 2004, in press.
Wu LY, Thompson D, Li GS, Hurt R, Huang H, Tiedje JM, Zhou J. Development and evaluation of functional gene arrays for detection of selected genes in the environment. Appl Environ Microbiol 2001. 67: 5780-5790.
Zhou, J, Thompson DK. Challenges in applying microarrays to environmental studies. Curr Opin Biotechnol 2002, 13:204-207.
Zhou, J. Microarrays for bacterial detection and microbial community analysis. Curr Opinion Microbiol 2003, 6:288-294.

* cited by examiner

*Primary Examiner*—Christopher M. Babic
(74) *Attorney, Agent, or Firm*—Quarles & Brady, LLP

(57) ABSTRACT

The present invention provides a method for quantitatively analyzing microbial genes, species, or strains in a sample that contains at least two species or strains of microorganisms. The method involves using an isothermal DNA polymerase to randomly and representatively amplify genomic DNA of the microorganisms in the sample, hybridizing the resultant polynucleotide amplification product to a polynucleotide microarray that can differentiate different genes, species, or strains of microorganisms of interest, and measuring hybridization signals on the microarray to quantify the genes, species, or strains of interest.

22 Claims, 8 Drawing Sheets

METHOD FOR ANALYZING MICROBIAL COMMUNITIES

CROSS-REFERENCE TO RELATED APPLICATIONS

This application claims the benefit of U.S. Provisional Ser. Application No. 60/541,620, filed Feb. 4, 2004.

STATEMENT REGARDING FEDERALLY SPONSORED RESEARCH OR DEVELOPMENT

This invention was made with United States government support awarded by the following agency: U.S. Department of Energy DE-AC05-00OR22725 and ERKP355. The United States has certain rights in this invention.

BACKGROUND OF THE INVENTION

Microorganisms play an integral and often unique role in ecosystem functions yet people know little about the dominant populations that presumably play vital roles in these functions, nor do people know much about how these populations differ with habitat. The greatest microbial diversity at small scales appears to reside in the soil, and hence soil microbial communities are among the most complex, diverse, and important assemblages in the biosphere. Analysis of genetic diversity in soil communities by DNA renaturation suggests that there are approximately $4-7\times10^3$ different genome equivalents per 30 g of soil, which, if extrapolated to species diversity, implies that there are at least $10^3$ or more species per g of soil.

Understanding the structure and composition of microbial communities and their responses to environmental perturbations such as toxic contamination, climate change, and agricultural and industrial practices is critical for the maintenance and restoration of desirable ecosystem functions. However, due to such extremely high diversity, the detection, characterization, and quantification of microbial communities in environmental samples are formidable tasks for environmental biologists. Traditional culture-based enrichment techniques for studying microbial communities have proven difficult and ultimately, provide an extremely limited view of microbial community diversity and dynamics, because the majority of naturally occurring species can not be cultured. The development and application of nucleic acid-based techniques largely eliminated the reliance on cultivation-dependent methods and consequently, greatly advanced the detection and characterization of microorganisms in natural habitats. However, the limitations of conventional nucleic acid-based detection methods prevent them from being readily adapted as high-throughput, cost-effective assessment tools for monitoring microbial communities.

DNA- or oligonucleotide-based microarray technology is a powerful functional genomics tool that allows researchers to view the physiology of a living cell from a comprehensive and dynamic molecular perspective (e.g., DeRisi et al. 1997, Khodursky et al. 2000, Spellman et al. 1998, Tao et al. 1999, Wei et al. 2001, Wodicka et al. 1997, and Ye et al. 2000). Compared to traditional nucleic acid hybridization with porous membranes, glass slide-based microarrays offer the additional advantages of high density, high sensitivity, rapid ("real-time") detection, lower cost, automation, and low background levels (Shalon et al. 1996). Target functional genes in environments tend to be highly diverse, and it is difficult, sometimes even experimentally impossible, to identify conserved DNA sequence regions for designing oligonucleotide probes for hybridization or primers for polymerase chain reaction (PCR) amplification. The microarray-based approach, however, does not require such sequence conservation, because all of the diverse gene sequences from different populations of the same functional group can be fabricated on arrays and used as probes to monitor their corresponding distributions in environmental samples.

Although microarray technology has been used successfully to analyze global gene expression in pure cultures (Lockhart et al. 1996, DeRisi et al. 1997, Schena et al. 1996, Richmond et al. 1999, Ye et al. 2000, Thompson et al. 2002, Liu et al. 2003, and Wodicka et al. 1997), it is not clear whether it can be successfully adapted for use in environmental studies with sufficient specificity, sensitivity, and quantitative power (Zhou and Thompson 2002). First, in environmental samples, target and probe sequences can be very diverse, and it is not clear whether the performance of microarrays used with diverse environmental samples is similar to that with pure culture samples and how sequence divergence affects microarray hybridization. Second, unlike pure cultures, environmental samples are generally contaminated with substances such as humic matter, organic contaminants, and metals, which may interfere with nucleic acids-based molecular detection. Third, in contrast to pure cultures, the retrievable biomass in environmental samples is generally low. It is not clear whether microarray hybridization is sensitive enough for detecting microorganisms in environmental samples. Finally, since microarray-based hybridization has inherently high variability, it is uncertain whether microarray-based detection can be quantitative. Environmental and ecological studies often require experimental tools that not only detect the presence or absence of particular groups of microorganisms but also provide quantitative data on their in situ biological activities.

Recently, various microarray formats such as functional gene arrays (Wu et al. 2001, Taroncher-Oldenburg et al. 2003, and Rhee et al. 2004, all of which are herein incorporated by reference in their entirety), community genome arrays (Wu et al. 2004 and Zhou, 2003, both of which are herein incorporated by reference in their entirety), and oligonucleotide arrays (Guschin et al. 1997a, Guschin et al. 1997b, Small et al, 2001, Rudi et al. 2000, Urakawa et al. 2002, Loy et al. 2002, Straub et al. 2002, and Wilson et al. 2002, all of which are herein incorporated by reference in their entirety) have been developed and for bacterial detection and microbial community analyses of environmental samples. However, as described above, these methods do not have sufficient sensitivity to allow quantitative analysis, especially the less abundant microorganisms, of the microbial communities. For example, the method disclosed in Rhee et al. 2004 requires DNAs from at least about $10^7$ cells to achieve reasonably strong hybridization using the 50-mer-based oligonucleotide microarrays.

Novel microarray-based methods that will allow quantitative and sensitive analysis of microbial communities, especially less abundant populations in natural environments, are desirable.

BRIEF SUMMARY OF THE INVENTION

The present invention provides a method for quantitatively analyzing microbial genes, species, or strains in a sample that contains at least two species or strains of microorganisms. The method involves using an isothermal DNA polymerase to randomly and representatively amplify genomic DNA of the microorganisms in the sample, hybridizing the resultant polynucleotide amplification product to a polynucleotide microarray that can differentiate different genes, species, or strains of microorganisms of interest, and measuring hybridization signals on the microarray to quantify the genes, species, or strains of interest. This quantitative method is sensitive in that individual species or strains whose genomic DNAs are in the 10 fg to 1 ng range can be quantified. So are the genes of the species or strains. In the case of *E. coli*, this means that as few as 2 bacterial cells and genes contained therein can be quantified.

The present invention further provides a buffer for conducting DNA amplification with an isothermal DNA polymerase. The buffer comprises any known or conventional buffer for DNA amplification supplemented with spermidine, one or more single strand binding proteins (SSB), RecA protein, or a combination of any of the foregoing.

The present invention further provides a buffer for conducting DNA hybridization. The buffer comprises any known or conventional hybridization buffer supplemented with spermidine, one or more RecA proteins, or both.

The present invention further provides a buffer for labeling DNA molecules, preferably with a fluorescent or radioactive material. The buffer comprises any known or conventional labeling buffer supplemented with spermidine, one or more RecA proteins, or both.

It is a feature of the present invention that the method provided here is quantitative and sensitive.

It is an advantage of the present invention that microorganisms and associated genes in complex environmental samples can be quantitatively analyzed.

It is another advantage of the present invention that the method is high throughput.

Other objects, advantages, and features of the present invention will become apparent from the following specification when taken in conjunction with the accompany drawings.

BRIEF DESCRIPTION OF THE SEVERAL VIEWS OF THE DRAWINGS

FIG. 5 shows representative and quantitative amplification and detection determined by: FIG. 5A community genome arrays and by FIG. 5B open reading frame (ORF) arrays. FIG. 5A shows genomic DNAs from 9 different species (A: *Peacocks denitrificans*; B: *Thauera aromatica*; C: *Rhodopseudomonas palustris*; D: *Shewanella oneidensis* MR-1; E: *Chrobactrum anthropi*; F: *Marinobacter* sp. D5-10; G: *Psedomonas* sp. C179; H: *Pseudomanas mendocina*; I: α-proteobacterium C1-4) that were mixed in equal quantity, amplified, labeled with Cy5 and then co-hybridized with non-amplified genomic DNA using community genome arrays. For individual genomes, no significant differences in the hybridization signal intensity (P=0.05) were observed between the amplified DNA and non-amplified genomic DNA. Significant correlations of the average signal intensity between the amplified DNA and the non-amplified DNA were obtained among the 9 microbial genomes. FIG. 5B shows open reading frame (ORF) arrays in which genomic DNAs from *S. oneidensis* MR-1 were diluted in series, amplified, labeled with Cy5 and co-hybridized with 2 Cy3-labeled non-amplified genomic DNAs. The linear relationships for some representative genes are shown in FIG. 5B; (SO4131, SO3234, SO1077, SO4136, and SO2637 are gene or open reading frame numbers of the genome of *Shewanella oneidensis* MR1 and they can be found in the GenBank of NCBI).

FIG. 6A shows a very strong linear relationship ($r^2$=0.91) of the signal intensity between the amplified and non-amplified DNAs ranging from 0.1 to 1000 ng was obtained. FIG. 6B shows a similar relationship between the signal intensities of the self genomic DNA and genomic DNA hybridization.

FIG. 7A shows a very strong linear relationship ($r^2$=0.93) between signal intensity and DNA concentrations ranging from 0.1 to 1000 ng was obtained. FIG. 7B shows a similar relationship between signal intensities of the self genomic DNA-genomic DNA hybridization).

DETAILED DESCRIPTION OF THE INVENTION

Figure 1:
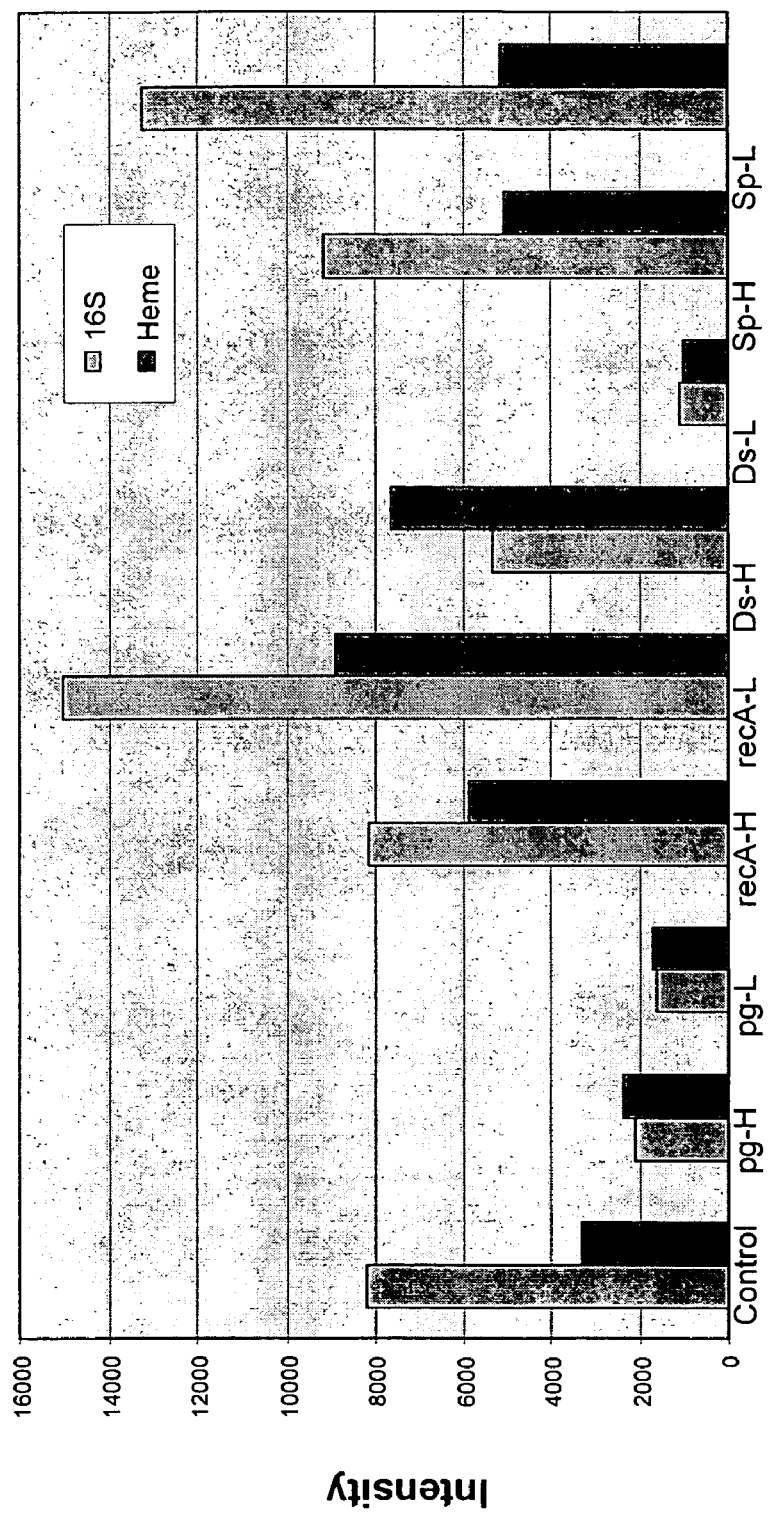
FIG. 1 shows an increase in hybridization sensitivity by addition of RecA and spermidine to hybridization solution (Pg: polyethylene glycol; recA: RecA protein; Ds: dextrin sulfate sodium salt; Sp: spermidine; H: added to hybridization reaction; L: added to labeling reaction).

The present invention is based on the inventors' discovery that the genomic DNAs of different species or strains of microorganisms in a complex sample, i.e., a sample that contains at least two, three, five, ten, fifty, one hundred, five hundred, one thousand, or ten thousand species or strains, can be representatively and thus quantitatively amplified, in terms of one species or strain relative to another, using an isothermal DNA polymerase. Importantly, the minor species or strains of a microbial community whose genomic DNAs are in the 10 fg to 1 ng range are representatively amplified. The inventors further discovered that for each species or strain, the isothermal DNA polymerase amplifies sufficient span of the genomic DNA so that the amplification product is suitable for distinguishing different species or strains of microorganisms when hybridized to a known polynucleotide microarray in the art designed for this purpose. The representative amplification in such a complex sample is also of a sufficient magnitude, even for the minor species or strains, to transfer into differential hybridization signal intensities on the microarray. In addition to the ability to quantify different species or strains of a microbial community, the method is also suitable for quantifying different genes in a microbial community when a suitable microarray such as a functional gene microarray is used.

In one aspect, the present invention relates to a method for quantifying individual genes, species or strains of microorganisms in a complex sample. The method involves randomly and representatively amplifying the whole microbial community genomic DNA, hybridizing the amplification product to a polynucleotide microarray that can differentiate different genes of interest or different species or strains of microorganisms of interest, and measuring hybridization signal to quantify the relative or absolute amount of different genes or different species or strains of the microorganisms. The present invention is especially useful for quantitatively analyzing genes and microorganisms in complex samples such as those obtained from the environment (e.g., soil, sediment, and ground water), a human or non-human animal, or a water or food source.

The sum of all microorganisms in a complex sample is referred to as a microbial community. By "quantifying," we mean that the relative or absolute amount rather than the mere presence or absence of two or more genes, species, or strains of microorganisms of interest is determined. By the relative amount of two genes, species, or strains of microorganisms, we mean the determination of whether one is more abundant than the other. The absolute amount of one, two, or more genes, species, or strains of microorganisms can be determined using, for example, suitable standard curves. The phrase "genes, species, or strains" means at least one of genes, species, and strains and the phrase "species or strains" means at least one of species and strains. When a community genome array that has the power to differentiate different species or strains of a microbial community is employed, the species or strains of the microbial community can be quantified. When a functional gene array that can differentiate different genes of a microbial community is employed, the genes of the microbial community can be quantified. In this regard, the quantification can be carried out without the information on which species or strains that the genes are from. When a microarray that has the power to differentiate both genes and species or strains of a microbial community, both can be quantified.

By representative amplification, we mean that the amount of amplified DNA from a less abundant species or strain is less than that of a more abundant species or strain. It is noted that when a microorganism has both chromosomal and non-chromosomal DNAs (e.g., mitochondria DNA), either chromosomal DNA or both chromosomal and nonchromosomal DNAs are amplified. In this regard, the term genomic DNA is used to refer to both chromosomal DNA by itself and a combination of chromosomal and nonchromosomal DNAs.

The quantitative method provided here is highly sensitive. As shown in the examples below, the method can detect a microorganism with only about 1 ng, 100 pg, 10 pg, 1 pg, 100 fg, or 10 fg of its genomic DNA. In the case of $E.$ $coli$ wherein on average one cell contains approximately 5 fg of genomic DNA, detection can be made with only about $2\times10^5$, $2\times10^4$, $2\times10^3$, 200, 20, or 2 cells. Using 5- and 10-fold increments of various amounts of starting genomic DNAs, the inventors show in the examples below that standard quantitation curves can be established for microorganisms whose genomic DNAs are in the picogram and nanogram ranges. It is expected that the method provided here can be used to determine the relative abundance of two species or strains of microorganisms if the amount of genomic DNA of one species or strain is 20% or less, 30% or less, 40% or less, 50% or less, 60% or less, 70% or less, or 80% or less of that of the other, particularly when the amount of genomic DNA of the less abundant species or strain is as low as about 1 ng, 100 pg, 10 pg, 1 pg, 100 fg, or 10 fg. It is understood that various standard curves can be employed to achieve more detailed and accurate quantitation.

The genomic DNA of the whole microbial community is randomly and representatively amplified with one of the so called isothermal DNA polymerases. Isothermal DNA polymerases are those which can amplify DNA sequences at a substantially constant temperature. Typically, the genomic DNA is extracted from the microorganisms before the amplification step is performed. The skilled artisan is familiar with the random DNA primers and other techniques involved in the amplification step. Many isothermal DNA polymerases are commercial available. Examples of isothermal DNA polymerases that can be used in the present invention include but are not limited to phi29 and Bst. Preferably, the amplification reaction is carried out in an amplification buffer that is supplemented with spermidine, one or more single strand binding proteins (SSB), RecA protein, or a combination of any of the foregoing. The supplementation, especially of spermidine and one or more single strand binding proteins, can increase the amplification efficiency and thus representation of minor microorganisms in a community that will not otherwise be sufficiently amplified.

The SSB used in the present invention can be any of the SSB known in the art (Chase et al, Ann. Rev. Biochem., 55:103-36, 1986, incorporated herein by reference in its entirety). SSB has the general property of preferential binding to single-stranded over double-stranded nucleic acids irrespective of the nucleotide sequence. Preferred SSB are those from $E.$ $coli$, fruit fly, $Xenopus$ $laevis$, gene 32 protein from T4 bacteriophage, gene 44/62 protein from T4 bacteriophage, T7 SSB, coliphage N4 SSB, adenovirus DNA binding protein (Ad DBP or Ad SSB), calf thymus unwinding protein (UP1), and a homologue of any of the foregoing from other species. The most preferred SSB is that from $E.$ $coli$.

The term "RecA protein" used herein means $E.$ $coli$ RecA protein and RecA-like recombinase proteins that are substantially equal to $E.$ $coli$ RecA protein and have all of or almost all the functions of $E.$ $coli$ RecA protein. Examples of the RecA proteins that can be used in the present invention include but are not limited to $E.$ $coli$ RecA protein (Shibata, T., et al., Methods in Enzymology, 100, 197, 1983), uvsX protein derived from T4 phage similar to $E.$ $coli$ RecA protein (Yonesaki, T., et al., Eur. J. Biochem., 148, 127, 1985), Rec protein derived from $Bacillus$ $subtilis$ (Lovett, C. M., et al., J. Biol. Chem., 260, 3305, 1985), Rec1 protein derived from $Ustilago$ (Kmiec, E. B., et al., Cell, 29, 367, 1982), RecA-like protein derived from yeast, a mouse, or a human (Shinohara, A., et al., Nature Genetics, 4, 239, 1993), and heat resistant RecA-like protein derived from thermophilic bacteria such as $Thermus$ $aquaticus$ (Angov, E., et al., J. Bacteriol., 176, 1405, 1994) or $Thermus$ $thermophilus$ (Kato, R., et al., J. Biochem., 114, 926, 1993). Among these proteins, the best characterized RecA protein is from $E.$ $coli$. As the RecA protein derived from $E.$ $coli$, not only the wild type but also a large number of its variant types (such as RecA803: Madiraju, M., et al., Proc. Natl. Acad. Sci. USA., 85, 6592, 1988 and RecA441: Kawashima, H., et al., Mol. Gen. Genet., 193, 288, 1984) can be used. The preferred RecA protein is the wild type RecA protein from $E.$ $coli$.

Polynucleotide microarrays such as DNA or RNA microarrays are well known in the art. A polynucleotide microarray typically contains at least two distinct polynucleotide molecules in terms of the polynucleotide sequence and the distinct polynucleotide molecules are located at different and known positions (locations) on the microarray substrate to form distinct detection elements. A position or detection element is an area on the microarray the hybridization signals from which are detected as a whole. Each polynucleotide molecule of the microarray may be present as a composition of multiple copies of the molecule on the substrate. The number of distinct polynucleotide molecules and positions or detection elements present on the microarray may vary, but is generally at least 2, usually at least 10, and more usually at least 20, where the number of different positions on the microarray may be as high as 50, 100, 500, 1,000, 10,000 or higher, depending on the intended use of the microarray. The positions of polynucleotide molecules present on the array surface are generally present as a pattern, where the pattern may be in the form of organized rows and columns of positions, e.g. a grid of positions.

Any polynucleotide microarrays that can differentiate the different genes, species, or strains of the microorganisms of interest can be used in the present invention for quantitatively analyzing the genes and microorganisms. Examples of such microarrays include but are not limited to functional gene arrays (Wu et al. 2001, Taroncher-Oldenburg et al. 2003, and Rhee et al. 2004, all of which are herein incorporated by reference in their entirety), community genome arrays (Wu et al. 2004 and Zhou, 2003, both of which are herein incorporated by reference in their entirety), and oligonucleotide arrays (Guschin et al. 1997a, Guschin et al. 1997b, Small et al, 2001, Rudi et al. 2000, Urakawa et al. 2002, Loy et al. 2002, Straub et al. 2002, and Wilson et al. 2002, all of which are herein incorporated by reference in their entirety).

In performing the step of hybridization between the polynucleotide amplification product of the whole microbial community and a polynucleotide microarray, it is preferred that the hybridization buffer employed be supplemented with spermidine, one or more RecA proteins, or both. The supplementation increases the hybridization sensitivity.

It is well within the capability of the skilled artisan to detect the hybridization event(s) between the amplification product and the polynucleotide microarray. For example, the polynucleotide molecules on the microarray can be labeled and after hybridization, the unhybridized, labeled molecules can be digested with a single strand-specific nuclease and removed from the microarray. It is preferred, however, that the polynucleotide amplification product be labeled for the detection of hybridization events.

Methods and materials that can be used to label DNA or RNA molecules for the purpose of the present invention are known in the art. In the examples below, a method of labeling the amplification product of the whole genomic DNA with Cy3 or Cy5 is described. However, other known labeling materials and methods can also be used. For example, other Cy dyes such as Cy3.5 and Cy5.5, Alexa fluorescent dyes, and radioactive isotopes such as $^{33}P$ can be used for labeling. Furthermore, a two-color fluorescent labeling strategy may be used in the present invention. The strategy is described in Ramsay 1998 and Shalon et al. 1996, both of which are incorporated by reference in their entireties. Preferably, the labeling reaction is carried out in a labeling buffer that is supplemented with spermidine, one or more RecA proteins, or both. The supplementation increases the labeling efficiency.

The present invention is not limited by the specific type of microorganisms being analyzed. Examples of the microorganisms that can be analyzed include but are not limited to viruses, bacteria, yeasts, fungi, and algae. More than one type of microorganisms can be analyzed simultaneously. In a preferred embodiment, different genes, species, or strains of bacteria from a sample are analyzed.

By way of example, but not limitation, examples of the present invention are described below.

Examples

Materials and Methods

Bacterial strains, environmental samples, and genomic DNA isolation: *Shewanella oneidensis* MR-1 (from inventors' laboratory), *Deinococcus radiodurans* R1 (from inventors' laboratory), *Rhodopseudomonas palustris* CGA009 (provided by Caroline Harwood, Department of Microbiology, University of Iowa), and *Nitrosomonas europaea* ATCC 19718 (provided by Daniel J. Arp, Botany and Plant Pathology Department, Oregon State University, Corvallis, Oreg.) were used for constructing whole genome cDNA microarray and also for constructing community genomic DNA arrays (CGA). Fourteen other distantly related bacteria strains were also used for constructing community genomic DNA arrays: α-proteobacterium C1-4, *Bacillus methanolicus* F6-2, *Marinobacter* sp. D5-10, *Halomonas variabilis* B9-12, *Pseudomonas* sp. G179, *Azoarcus tolulyticus* Td1 were from inventors' collection or marine isolates; and *Thauera aromatica, Paracoccus denitrificans, Achromobacter xylosoxidans, Rhizobium meliloti, Ochrobactrum anthropi, Azospirillum brasilense, Pseudomonas mendoxina* ATCC 25411, *Rhodopseudomopnas* were from the American Type Culture Collection (ATCC, Manassas, Va.). All of the strains were grown in Luria-Bertani broth except that *Nitrosomonas europeae* was grown in *Nitrosomonas europeae* medium and *Rhodopseudomonas palustris* was grown in nutrient broth. Cells were harvested at the exponential phase and frozen at −80° C.

To evaluate the performance of the whole community genome amplification in microbial community analysis, ground water samples obtained from the Field Research Center (FRC) site of Depart of Energy (DOE) NABIR program at Oak Ridge Reservation, Oak Ridge, Tenn., were used. The FRC site includes three areas of contaminated soil and groundwater and one uncontaminated background area that contains soils similar to those found in the contaminated areas. The site contained four unlined ponds that received approximately 10 million liters of liquid nitric acid and uranium bearing wastes per year for approximately 30 years until closure in 1984. The waste ponds contribute to both sediment and groundwater contamination with nitrate, uranium, heavy metals, and a variety of low level organic contaminants. A full description can be found at the FRC website available on the world-wide web. Groundwater samples were from five wells. Wells FW-010 and FW-024, located in Area 3, are 32.5 m apart and are approximately 20 m from the former waste pond. Well FW021 is 27 m from the waste pond embankment in area 1 and is approximately 130 m from the wells in area 3. Well FW-003 is located in area 2. Area 2 is approximately 275 m down gradient from the waste ponds in area 1 and area 3. Well FW-300 is located in the uncontaminated background area, approximately 6 km northwest of the source ponds. Water was collected from a screened interval below the water table at each of the six wells on the same day (Apr. 2, 2003). Another groundwater sample was collected from well FW-029 located in area 1 that has been experimentally enriched with ethanol to stimulate the anaerobic microbial community.

The genomic DNAs of the pure cultures were isolated using previously described protocols (Sambrook et al., 1989). All genomic DNA samples were treated with RNase A (Sigma, St. Louis, Mo.) and analyzed on agarose gels stained with ethidium bromide prior to microarray fabrication. Groundwater samples were collected and transported to the inventors' laboratory in amber glass bottles. Bacteria were harvested by centrifugation (10,000× g, 4° C. for 30 min) and the pellets were stored at −80° C. until DNA extraction. The cell pellets were re-suspended in a lysis buffer and the cells disrupted with a previously described grinding method (Zhou et al., 1996; 1997) and purified by gel electrophoresis plus mini-column (Wizard DNA Clean-Up system, Promega, Madison, Wis.). DNA concentration was determined in the presence of ethidium bromide by fluorometric measurement of the excitation at 360 nm and emission at 595 nm using a HTS700 BioAssay Reader (Perkin Elmer, Norwalk, Conn.).

Whole community or genome DNA amplification using phi 29 DNA polymerase: A Templiphi 500 Amplification kit (Amersham Biosciences, Piscataway, N.J.) was used for whole genome amplification of all genomic DNAs. 1 µl of genomic DNA (10 fg to 100 ng) was mixed thoroughly with 50 µl of sample buffer containing random hexamers in a 0.2 ml PCR tube and set at room temperature for 10 min. A Templiphi premix was made by combining 50 µl of reaction buffer, containing salts and deoxynucleotides, and 2 µl enzyme mix, containing Phi 29 DNA polymerase and additional random hexamers, for each reaction in a separate tube. 50 µl of Templiphi premix was transferred to and mixed with the DNA sample. The reactions were incubated at 30° C. for varying lengths of time. An optimized incubation of 2 hours was determined by measuring DNA amount amplified on a gel every half hour for 12 hours. Additives tested for improving amplification performance (*E. coli* RecA protein, 260 ng/µl; *E. coli* single strand binding protein (SSB), 267 ng/µl; and spermidine, 0.1 mM; betaine, 1M; DMSO, 1%) were tested separately or jointly. All subsequent experiments included 0.1 mM of spermidine and 267 ng/µl of SSB in the optimized protocol. Reactions were stopped by heating at 65° C. for 10 min and products were analyzed in 1% agarose gels.

Microarray construction and specifications: Whole genome microarrays of *S. oneidensis* MR-1 (approximately 4.9 Mb), a metal reducing bacterium, *D. radiodurans* (3.2 Mb), a radiation-resistant bacterium, *R. palustris* (4.8 Mb), a photosynthetic bacterium, and *N. europaea*, an ammonium oxidizing bacterium (2.7 Mb) were constructed as described previously (Gao et al. 2004 and Liu et al. 2003) for evaluating the representation of the whole community genome amplification. In total, 3046, 4700, 4508, and 2354 ORF-probes were designed for these four genomes respectively. About 90-95% of the ORFs were amplified for all genomes. 50 mer oligonucleotides were designed for the genes, which were not amplified. The total gene coverage of the four whole genome arrays ranged within 95-99%. PCR products or 50 mer oligoes in 50% DMSO were spotted in duplicates onto amino propyl silane coated Ultra GAPS glass slides (Corning, Corning, N.J.) or Superamine glass slides (TeleChem International, Inc., Sunnyvale, Calif.) and the printing quality was evaluated by direct scanning of the slides, PicoGreen (Molecular Probes Inc., Eugene, Oreg.) staining and direct genomic DNA hybridization. The arrays were post-processed following the instruction of the manufacturers.

An array consisting of whole genomic DNA from 18 bacteria strains was constructed to determine the representation and the quantitation of the whole community genome amplification for an artificial microbial community composed of multiple microbial species whose GC content vary in a range of 43-68%. Five *S. cerevisiae* genes were included in this array as the negative controls. All 23 probes (including negative controls) were arranged as a matrix of 15 rows×2 columns (denoted columns a-b). Genomic DNA samples were prepared for deposition, printed and postprocessed as described above. Each glass slide contained 3 replicates of genomic DNA from individual strains.

An oligonucleotide functional gene array for monitoring bioremediation and nutrient cycling was constructed using the methods described in Rhee et al., 2004 and used for the evaluation of whole community genome amplification. This oligo-based microarray contained probes from various groups of genes involved in organic contaminant degradation, metal resistance and nutrient cycling. A total of 2006 oligonucleotide probes were printed in duplicate on each microarray slide. The information on probe sequence, melting temperature, their organism origin and gene function can be found at the Oak Ridge National Laboratory's Environmental Sciences Division website available on the world-wide web. The probes from six human genes and four plant genes were included on the microarrays as negative or qualitative controls. In addition, two highly conserved 16S rRNA gene probes were included as positive control probes. Probes were prepared for microarray deposition, printed and postprocessed as described above.

DNA labeling and hybridization: Genomic DNA or DNA amplified from small amount of genomic DNA by whole community genome amplification was fluorescently labeled using the random priming method and purified as described previously (Wu et al., 2001). All microarray experiments were performed in triplicate, unless otherwise noted, to enable statistical analyses. The hybridization solution contained denatured fluorescently labeled genomic DNA, 50% formamide, 3×SSC (1×SSC contains 150 mM NaCl and 15 mM sodium citrate), 2 µg of unlabeled herring sperm DNA (Promega, Madison, Wis.), and 0.3% SDS in a total standard volume of 30 µl. Hybridization solutions were heated at 95° C. for 3 min and kept warm in a 50° C. incubator. Microarray slides, coverslips and pipette tips were warmed up and kept warm also in an incubator prior to the hybridization. Microarrays were placed into a self-contained flow cells (Telechem International) into a 50° C. water bath immediately for overnight hybridization. Following hybridization, coverslips were removed in pre-warmed washing buffer (1×SSC-0.2% SDS) and then washed sequentially for 5 min in 1×SSC-0.2% SDS and 0.1'SSC-0.2% SDS and for 30 sec in 0.1×SSC prior to being air-dried in the dark.

Microarray scanning and data analysis: A ScanArray® 5000 Microarray Analysis System (PerkinElmer, Wellesley, Mass.) was used for scanning microarrays. A quick scan at a resolution 50 µm was performed prior to the real scanning at a resolution of 10 µm and laser power and photomultiplier tube (PMT) gain were adjusted to avoid saturation of spots and to make the two channels of fluorescence comparable. Scanned image displays were saved as 16-bit TIFF files and analyzed by quantifying the pixel density (intensity) of each hybridization spot using the software of ImaGene™ version 5.0 (Biodiscovery, Inc., Los Angeles, Calif.). Mean signal intensity was determined for each spot and the local background signal was subtracted automatically from the hybridization signal of each spot. Fluorescence intensity values for all replicates of the negative genes, 10 *Arabidopsis thaliana* genes for the 4 whole genome arrays, 5 yeast genes for the small community genomic DNA arrays, or the human genes for the functional gene arrays (FGA) were averaged and then subtracted from the background-corrected intensity values for each hybridization signal. The signal-to-noise ratio (SNR) was also calculated based on the formula following of Verdnik et al. (2002) where: SNR=(Signal Intensity−Background)/Standard Deviation of Background. Spots with SNR lower than 3 were removed from further analysis. To make the different treatment of the experiments for testing additives, different genomes, template concentrations, and mixtures comparable, the removal of poor spots was based on the unamplified genomic DNA.

Statistical analysis and indices: Microarray data was subjected to outlier detection and removal, and normalization. The outliers, represented by the data points that were not consistently reproducible and had a disproportionately large effect on the statistical result, was detected and removed at p=0.01, which means when the absolute value of a data point minors the mean was large than 2.90 σ, the data point was determined as an outlier and removed. The hybridization ratios of the whole community genome amplification-amplified DNA to that of the un-amplified genomic DNA were normalized by reference mean, based on the hypothesis that the gene representation of an amplified DNA should be equal to its template un-amplified genomic DNA. For the microarray data of community genomic DNA arrays and 50-mer oligonucleotide arrays, normalizations were performed by the mean of the spiked internal positive control genes. After the removal of outliers and normalization, data points of a gene was averaged, and further statistical analysis was performed. A standard t test was performed so that a two-tailed probability of a mean deviating from 1.0 could be calculated and used to determine the significant difference between amplified DNA and un-amplified genomic DNA for each gene. A percentage of the significant genes was calculated based on the t test results and used as one of the indices defining the performance of whole genome amplification. Two other indices, $D_j^{total}$ and the fold changes of hybridization signal intensity were also computed for the evaluation of evenness, or gene representation of the whole community genome amplification. $D_j^{total}$ is the average distance of the log ratio from the reference point, 0. It is similar to Euclidean distance. $D_j^{total}$ will be equal to 0 if there is no bias. $D_j^{total}$ describes the bias. The smaller the $D_j^{total}$ is, the smaller the bias is. The equation to calculate $D_j^{total}$ is $$D_j^{total} = \sqrt{\sum_{i=1}^{N} (LR_{i,j} - 0)^2 / N_j} = \sqrt{\sum_{i=1}^{N} (LR_{i,j})^2 / N_j}$$

where $LR_{i,j}$ is the log ratio of i gene in a specific treatment, j; $N_j$ is the gene number of effective in the treatment j. The percentage of genes which had two, three, and four fold changes in hybridization signal intensity were also calculated, giving another view of the representation of the whole community genome amplification. For the analysis of microarray data from FRC samples, cluster analysis was performed using the pair-wise average-linkage hierarchical clustering algorithm (Eisen et al., 1998) provided in CLUSTER software available on the Eisen Lab-Lawrence Berkeley National Lab website on the world-wide web, and the results of hierarchical clustering were visualized using TREEVIEW software available on the Eisen Lab-Lawrence Berkeley National Lab website on the world-wide web. Principle component analysis (PCA) analysis and canonical analysis were also performed using SYSTATE 10.0 and SAS for comparing the microarray data of the FRC samples and the chemical data of the sampling sites.

Results

Increase of hybridization sensitivity by addition of RecA and spermidine: Various additive reagents were added to labeling and hybridization buffers as described in the materials and methods to test their efficacy for increasing hybridization sensitivity. The addition of RecA protein (260 ng/µl) and spermidine (0.1 mM) to the labeling reaction and the hybridization solution resulted in a threefold increase in fluorescence signal intensity (FIG. 1). Other additives (dextran sulfate sodium, polyethylene glycol, E. coli single-strand binding protein) did not improve hybridization sensitivity.

Figure 2:
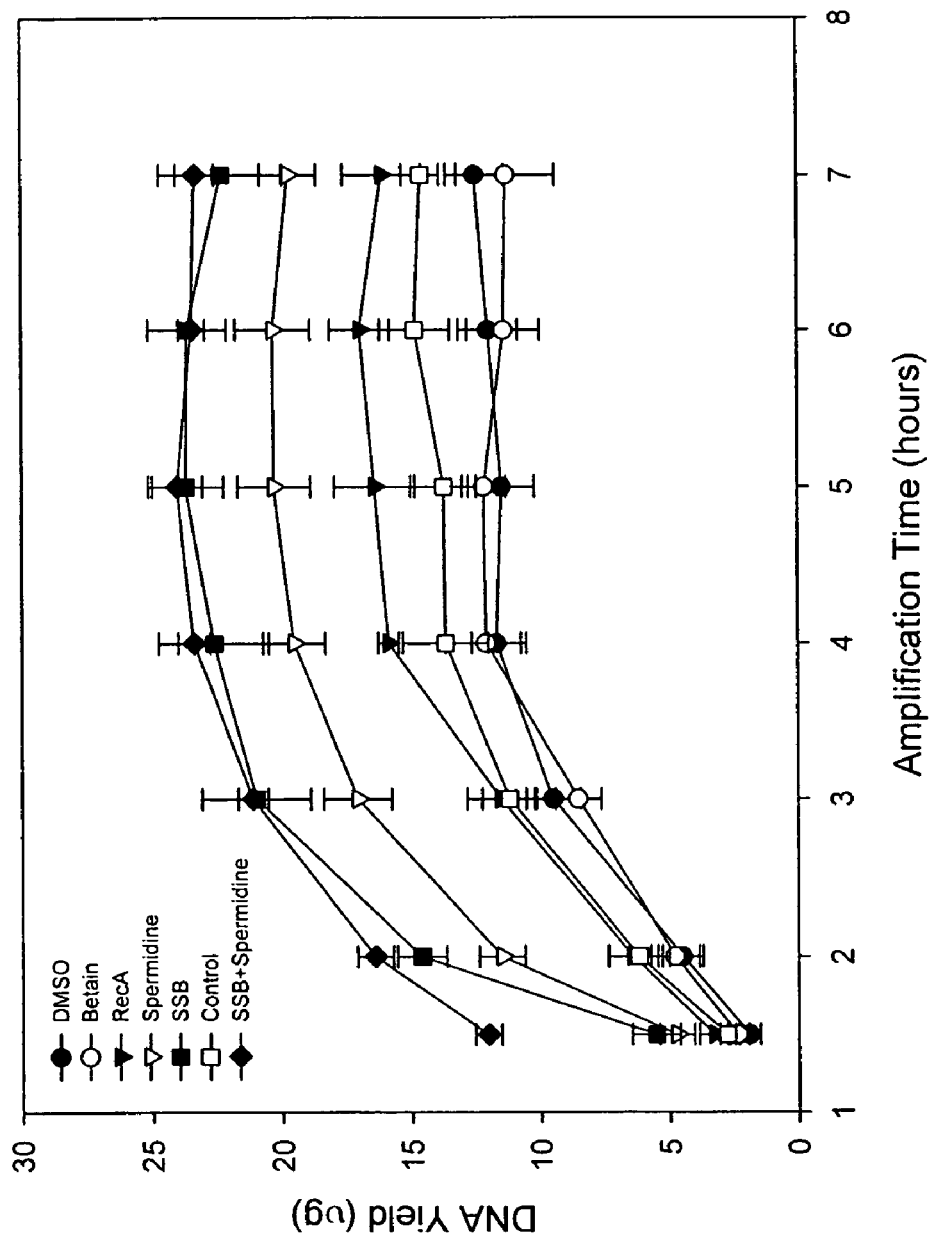
FIG. 2 shows the effects of various additive reagents on efficiency of isothermal DNA polymerase amplification.

Increase of amplification efficiencies and representations by addition of SSB and spermidine: To improve amplification efficiency, reaction buffers that contained various additive reagents were evaluated. One ng of Rhodopseudomonas palustris genomic DNA was amplified in triplicate with commercial buffer containing different additive reagents and with commercial buffer containing no additive reagents as a reference (reference buffer). Compared to the reference buffer, the modified buffer containing SSB or spermidine significantly improved DNA yields (49-66%) (FIG. 2), whereas the buffer containing dimethyl sulfoxide (DMSO) or betaine significantly decreased the amplification efficiency (11-14%). A slight increase in DNA yield was observed with the buffer containing recA protein (16%; FIG. 2) and the highest yields were obtained with the buffer containing SSB. In addition, the amplification reached a plateau earlier with the buffers containing SSB or spermidine (about 4 hours) than the buffer containing betaine, DMSO or no additive reagents (approximately 5 hours; FIG. 2).

Since both SSB and spermidine significantly improved DNA yields, the buffer containing both SSB and spermidine was further tested. As shown in FIG. 2, the amplification efficiency was slightly higher for the buffer containing both SSB and spermidine than that with SSB alone.

To determine the effects of the additive reagents on sequence representation in the amplified DNAs, microarray hybridization with the ORF arrays was performed and the hybridization data were analyzed as described above. Considerable improvements in sequence representation in the amplified DNAs were obtained with the buffer containing SSB or spermidine. For instance, the total representational bias (D) for the buffer containing SSB or spermidine was 1.5-2 fold lower than for the commercial buffer without additive reagents, and even lower or comparable to the representational bias observed in hybridizations with non-amplified genomic DNA (Table 1). The proportions of the genes whose hybridization ratios were significantly different from the reference point of 1 were also considerably less for the buffer containing SSB (3.5%) or spermidine (0.7%) than the commercial buffer (8.9%) (Table 1). In addition, the proportions of genes whose hybridization signal ratios (amplified DNA/genomic DNA) were less than 2 fold different were substantially less for the modified buffer containing SSB (0.2%) or spermidine (0.3%) than the reference buffer (1.5%). These results show that the use of SSB or spermidine substantially improved sequence representations. However, compared to the commercial reference buffer, little effect on the sequence representation was observed for the buffer containing recA protein.

TABLE 1

Effects of additives on amplification and hybridization performance.

| | Additives | | | | |
|---|---|---|---|---|---|
| Parameter | RecA | SSB | Spermidine | Reference buffer (no additives) | gDNA (non-amplified DNA) |
| Total effective gene number (N) | 4865 | 4798 | 4855 | 4850 | 4670 |
| Representational bias ($D^{total}$) | 0.102 | 0.069 | 0.055 | 0.107 | 0.078 |
| Proportions of genes significantly different from ratio 1 at P = 0.01 ($SDG_{0.01}$) | 0.043 | 0.035 | 0.007 | 0.089 | 0.024 |
| % of >1.5 folds | 6.968 | 2.334 | 1.462 | 8.103 | 4.026 |
| % of >2 folds | 1.233 | 0.229 | 0.268 | 1.546 | 0.514 |
| % of >3 folds | 0.247 | 0.000 | 0.021 | 0.206 | 0.000 |
| % of >4 folds | 0.021 | 0.000 | 0.021 | 0.062 | 0.000 |

Figure 3:
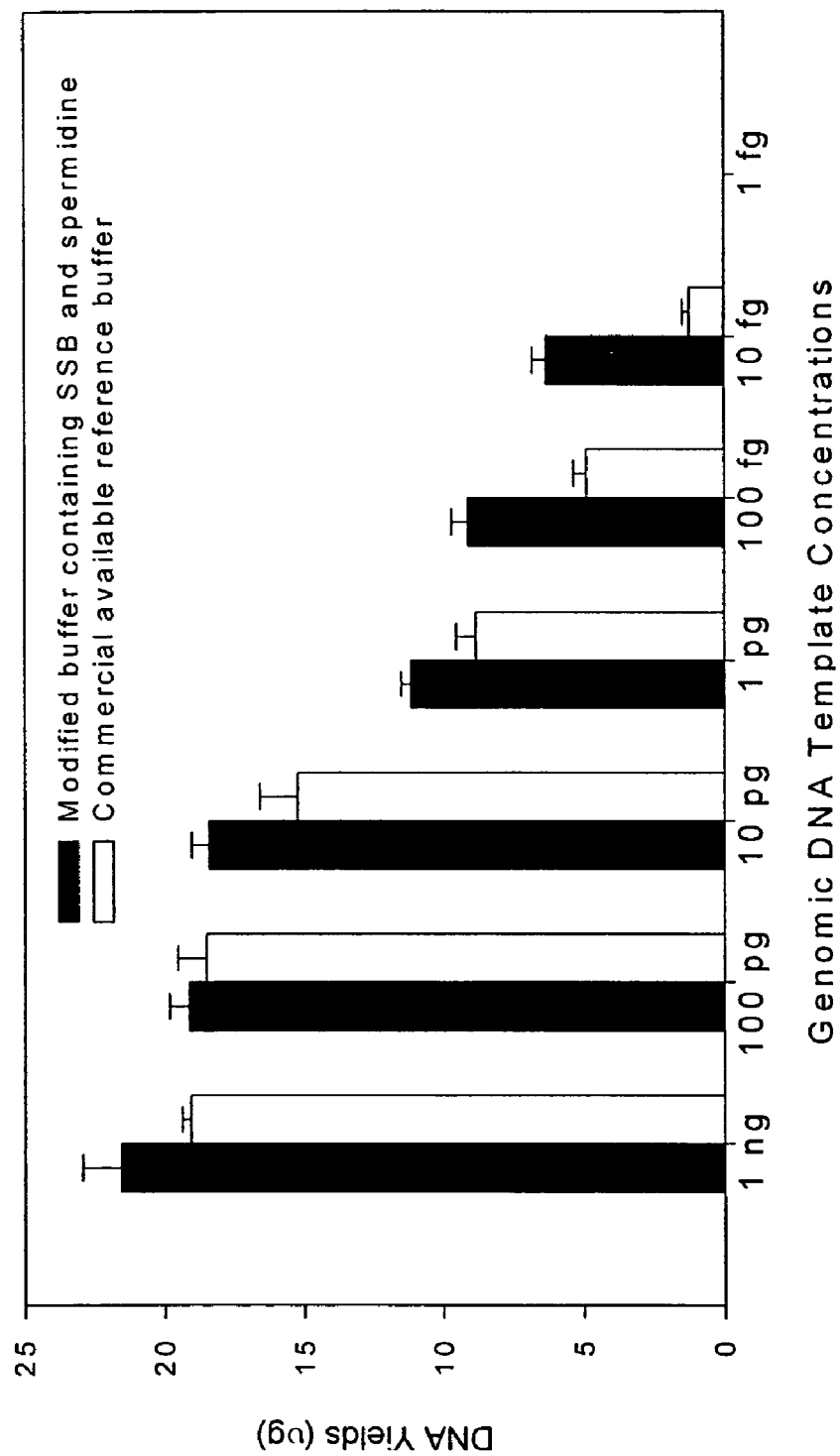
FIG. 3 shows the effects of various additive reagents on amplification sensitivity of whole community genome amplification.

Increase of amplification sensitivity: The amplification sensitivity was determined using a series of 10 fold genomic DNA dilutions ranging from 1 fg to 1 ng. At the genomic DNA template concentration of 100 fg, approximately twice as many DNAs were obtained with the modified buffer containing SSB and spermidine (9.13±0.57 µg after 4 hours) than with the commercial reference buffer (4.90±0.45 µg; FIG. 3). At a concentration of 10 fg of template genomic DNA, little amplified DNA was obtained with the reference buffer (0.52±0.24 µg after 4 hours), but approximately 7 µg of DNA was obtained after 4 hours using the modified buffer. No DNA was observed at the template DNA concentration of 1 fg (FIG. 3) or for the control sample. These results show that the amplification sensitivity is 10 fold higher with the modified buffer than with the commercial reference buffer and the amplification sensitivity is approximately 10 fg DNA with the modified buffer containing SSB and spermidine.

Figure 4:
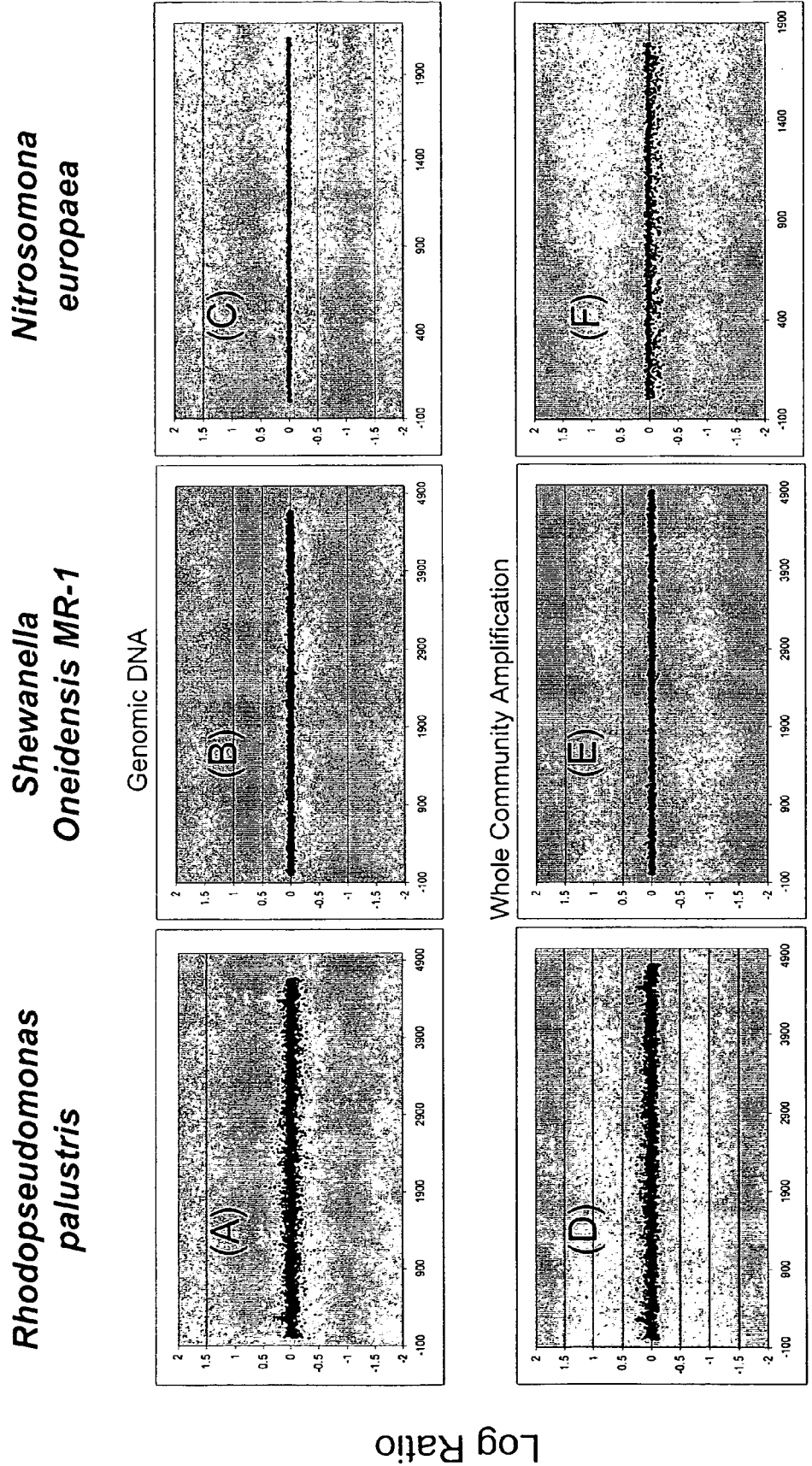
FIG. 4 are scatter plots showing representational amplification biases with three different species. Genomic DNA from *R. palustrus*, *S. oneidensis* and *N. europaea* were amplified and labeled with Cy5; non-amplified genomic DNA was labeled with Cy3. The Cy5/Cy3 ratio was aligned along a line corresponding to the 1:1 hybridizations of non-amplified DNAs from *R. palustris* (FIG. 4A), *S. oneidensis* (FIG. 4B) and *N. europaea* (FIG. 4C). The Cy5/Cy3 ratios of amplified DNAs to non-amplified DNAs from whole communities (FIGS. 4D, E and F) show slight scatter, suggesting slight over-representation and under-representation of some ORFs.

Representative amplification with different species: To determine whether isothermal DNA polymerase amplification is representative, 10 ng genomic DNA from *Rhodopseudomonas palustrus*, *Shewanella oneidensis* and *Nitrosomonas europaea* containing different GC content and genome size were amplified for 4 hours using the modified buffer containing SSB and spermidine. The amplified DNA (18-25 µg) was labeled with Cy5 and the non-amplified genomic DNA was labeled with Cy3. Then, 2 µg of the Cy5-labeled amplified DNA was co-hybridized with 2 µg Cy3-labeled genomic DNA. To avoid potential dye bias, dye switching was performed. As a control, two samples of 2 µg of genomic DNA were labeled with Cy5 and Cy3, respectively and then hybridized together with the whole genome arrays. Poor spots and outliers were removed based on non-amplified genomic DNA hybridization. The signal intensity data were normalized and plotted as shown in FIG. 4. The Cy5/Cy3 ratio was aligned along a line corresponding to the 1:1 hybridizations of non-amplified DNAs from *R. palustrus* (FIG. 4A), *S. oneidensis* (FIG. 4B) and *N. europaea* (FIG. 4C). The Cy5/Cy3 ratios of amplified DNAs (4 hours) to non-amplified DNAs show slight scatter, suggesting slight over-representation and under-representation of some ORFs (FIGS. 4D, E, F). For *S. oneidensis* and *R. palustrus*, the over-representational bias in amplified DNA was slightly higher than the under-representational bias (Table 2). However, the over-representational bias for *N. europaea* in amplified DNA was considerably lower than the under-representational bias.

TABLE 2

Representative amplification of different microbial genomes.

| | Rhodopseudomonas palustris | | Nitrosomonas europaea | | Shewanella oneidensis | |
|---|---|---|---|---|---|---|
| Parameter | gDNA (not amplified) | RCA (amplified) | gDNA (not amplified) | RCA (amplified) | gDNA (not amplified) | RCA (amplified) |
| Total effective gene number (N) | 4670 | 4798 | 2116 | 1797 | 4683 | 4925 |
| Representational bias ($D^{total}$) | 0.078 | 0.069 | 0.013 | 0.074 | 0.024 | 0.021 |
| Proportions of genes significantly different from ratio 1 at P = 0.01 ($SDG_{0.01}$) | 0.024 | 0.035 | 0.002 | 0.020 | 0.004 | 0.002 |
| % of >1.5 folds | 4.026 | 1.462 | 0.000 | 4.508 | 0.000 | 0.000 |
| % of >2 folds | 0.514 | 0.229 | 0.000 | 0.000 | 0.000 | 0.000 |
| % of >3 folds | 0.000 | 0.000 | 0.000 | 0.000 | 0.000 | 0.000 |
| % of >4 folds | 0.000 | 0.000 | 0.000 | 0.000 | 0.000 | 0.000 |

To more accurately evaluate the amplification performance, various quantitative indexes were calculated and compared between hybridizations with the amplified DNA and non-amplified genomic DNA. For R. palustris, the average total representational biases (D) in the amplified DNA (0.0686) was very similar or slightly lower than that in non-amplified genomic DNA (0.0781) (Table 2), indicating that the representational bias is mainly from microarray hybridization rather than from DNA amplification. Also, while the over-representational bias is very similar between the amplified DNA and non-amplified DNA, the under-representational bias in amplified DNA is slightly lower than non-amplified genomic DNA. In addition the proportions of the genes whose hybridization ratios were significantly different from the reference point at P=0.01 were slightly higher for amplified DNA (3.5%) than non-amplified genomic DNA (2.3%) (Table 2). However, the proportions of the genes whose hybridization signal ratios (amplified DNA/genomic DNA) having less than 2 fold differences were slightly lower for amplified DNA (0.2%) than for non-amplified genomic DNA (0.5%). Very similar results were observed for S. oneidensis (Table 2). However, no genes were observed whose hybridization signal ratios (amplified DNA/genomic DNA) had greater than 2 fold differences.

In contrast to S. oneidensis and R. palustris, the average total representational bias for N. europaea was about 6 times higher in amplified DNA than in non-amplified genomic DNA. Both under- and over-representational biases were substantially higher in amplified DNA than in non-amplified genomic DNA (Table 2). Also, the proportions of the genes whose hybridization ratios were significantly different from the reference point at P=0.01 were considerably higher for amplified DNA (2.0%) than non-amplified genomic DNA (0.2%) (Table 2). However, no genes were observed whose hybridization signal ratios (amplified DNA/genomic DNA) had larger than 2 fold differences.

In summary, the results using different quantitative indexes with different bacterial species show that whole community genome amplification using isothermal DNA polymerase is highly representative.

DNA concentration-dependent representative amplification: Since the amplification process is random, representational bias could be dependent on template DNA concentrations. To evaluate the effects of DNA template concentrations on representational biases, genomic DNA from R. palustris from 10 μg to 10 ng were amplified (approximately 0.3, 1.5, 18, 21, and 25 μg after 4 hours) and the normalized ratios of amplified DNA to non-amplified DNA were analyzed as described above. As shown in Table 3, the template DNA concentration has dramatic effects on overall average representational biases. For example, the overall average representational bias is more than 3 times higher with the 1 ng DNA template than with the 10 ng DNA template (Table 3). While the overall average representational biases were similar when 10 and 100 pg DNA were used, the biases were more than 2 times higher then with 1 ng DNA. In addition, the proportions of the genes whose hybridization ratios were significantly different from the reference point at P=0.01 increased as the DNA template concentrations decreased (Table 3). Around 30% of the ORFs were significantly different (P=0.01) at the template concentrations of 10 and 100 pg. The majority of the ORFs (69-77%) showed greater than 2 fold differences at the lower template concentrations (100 and 10 fg), whereas only small portions of the ORFs (0.2-18%) showed less than 2 fold differences at 10 and 1 ng. About 33-34% of the genes showed larger than 4 fold differences at the template concentrations of 10 and 100 fg, whereas only less than 1.3% of the ORFs showed larger than 4 fold differences at the template concentrations of 1 and 10 ng.

TABLE 3

Effects of DNA template concentrations on representative amplification. DNA template concentrations (Rhodopseudomonas palustris)

| Parameter | 10 ng | 1 ng | 100 pg | 10 pg |
|---|---|---|---|---|
| Total effective gene number (N) | 4798 | 4838 | 4840 | 4724 |
| Representational bias ($D^{total}$) | 0.069 | 0.227 | 0.545 | 0.592 |
| Proportions of genes significantly different from ratio 1 at P = 0.01 ($SDG_{0.01}$) | 0.035 | 0.139 | 0.294 | 0.322 |
| % of >1.5 folds | 1.462 | 40.099 | 81.798 | 76.152 |
| % of >2 folds | 0.229 | 17.611 | 68.905 | 76.884 |
| % of >3 folds | 0.000 | 4.361 | 48.946 | 52.942 |
| % of >4 folds | 0.000 | 1.385 | 32.500 | 34.462 |

Representational amplification with mixed species of equal concentrations: To determine whether representational amplification with a mixed community DNA can be achieved, equal quantities of template DNAs (1 or 10 ng from S. oneidensis, R. palustrus and N. europaea were mixed, amplified (approximately 18 μg after 4 hours) and subjected to hybridization and analysis as described above. At the DNA template concentrations of 30 ng (10 ng from each species), the overall average representational bias in N. europaea (0.1609) was about 2 times as much as that in R. palustrus (0.0884) and about 4 times as much as that in S. oneidensis (0.0447). The overall average representative bias for the mixed, individual genomes was about 1.3 to 2.2 times higher than when other genomic DNAs were absent, suggesting that the presence of DNA from other species has an effect on the amplification of individual genomes. However, the proportions of the genes whose hybridization ratios were significantly different from the reference point at P=0.01 were very comparable in mixed DNA populations (0.5-5.3%, Table 4) to those observed in the absence of other DNA templates (0.2-3.5%, Table 2). Also, very small portions of the genes (0.1-6.3%) showed 2 fold differences, but none of the genes showed 3 fold differences. These results are comparable to those observed in the absence of other DNA templates and indicate that although the presence of other DNA templates has effects on representative amplification, their impacts do not appear to be significant.

TABLE 4

Representational amplification and detection of equally mixed genomic DNAs (R.p. = *Rhodopseudomonas palustris*, S.o. = *Shewanella oneidensis*, and N.e. = *Nitrosomonas europaea*).

| Parameter | Genomic DNAs (10 ng each) | | | Genomic DNAs (1 ng each) | | |
|---|---|---|---|---|---|---|
| | R.p. | S.o. | N.e. | R.p. | S.o. | N.e. |
| Total effective gene number (N) | 4445 | 4942 | 1861 | 4733 | 5015 | 1555 |
| Representational bias ($D^{total}$) | 0.088 | 0.045 | 0.161 | 0.187 | 0.272 | 0.243 |
| Proportions of genes significantly different from ratio 1 at P = 0.01 ($SDG_{0.01}$) | 0.028 | 0.005 | 0.053 | 0.142 | 0.119 | 0.106 |
| % of >1.5 folds | 5.489 | 0.648 | 29.178 | 32.052 | 50.508 | 48.360 |
| % of >2 fold | 0.290 | 0.140 | 6.130 | 9.210 | 26.400 | 23.090 |
| % of >3 fold | 0.020 | 0.020 | 0.000 | 1.650 | 7.700 | 4.310 |
| % of >4 fold | 0.020 | 0.020 | 0.000 | 0.550 | 3.090 | 0.260 |

At the total DNA template concentrations of 3 ng (1 ng from each species), the differences of the average overall representational biases among *R. palustris* (0.1865), *S. oneidensis* (0.2717) and *N. europaea* (0.2433) were considerably less than those when 10 ng DNA from each species were mixed (Table 4), but the magnitudes of the average overall representational biases were substantially higher (approximately 1.5-6 fold) at the mixed DNA concentrations of 3 ng than at 30 ng. About 10-14% of the genes had hybridization ratios significantly different from the reference point at P=0.01, which is substantially higher than those at the total DNA concentrations of 30 ng (0.5-5.3%) (Table 4). Although about 9-26% of the genes showed more than 2 fold differences, the proportions of the genes showing 3 fold differences were 1.7-7.7%. These results indicate that DNA concentrations can have significant impacts on the overall performance of the isothermal DNA polymerase-based microarray hybridizations.

To further understand the effects of mixed templates on the isothermal DNA polymerase amplification performance, the hybridization ratio data for *R. palustris* at DNA concentrations of 1 ng from different experiments were further compared. As shown in Tables 3 and 4, the overall average representational bias, the proportions of the genes showing significantly different from reference point and the proportions of the genes having less than 2, 3, or 4 fold differences were very similar or even less when using mixed DNA templates than when using single-species DNA templates. These results indicate that the presence of non-target DNA templates could improve the amplification performance at low DNA template concentrations.

Representational amplification with species mixed at unequal concentrations: In natural microbial communities, not all species are equally abundant. To determine the representative bias within the context of environmental application, genomic DNA from *R. palustris* (10 ng), *S. oneidensis* (1 ng) and *N. europaea* (0.1 ng) were mixed, amplified (approximately 17 μg in total after 4 hours), hybridization in triplicate, and analyzed as described above. The overall average representational bias increased as the DNA concentrations decreased (Table 5). Although the magnitude of the representational biases were considerably higher than those observed in other experiments, the proportions of the genes showing significant differences from the reference points were similar. These results suggest that the amplification of mixed DNAs of unequal concentrations is fairly representative.

TABLE 5

Representational amplification and detection of unequally mixed genomic DNAs.

| Parameter | *Rhodopseudomona palustris* (10 ng) | *Shewanella oneidensis* (1 ng) | *Nitrosomonas europaea* (100 pg) |
|---|---|---|---|
| Total effective gene number (N) | 4407 | 3539 | 1907 |
| Representational bias ($D^{total}$) | 0.123 | 0.337 | 0.449 |
| Proportions of genes significantly different from ratio 1 at P = 0.01 ($SDG_{0.01}$) | 0.023 | 0.093 | 0.046 |
| % of >1.5 folds | 9.806 | 59.405 | 55.177 |
| % of >2 fold | 2.178 | 36.762 | 43.314 |
| % of >3 fold | 0.182 | 16.587 | 24.541 |
| % of >4 fold | 0.023 | 7.884 | 14.840 |

Figure 5:
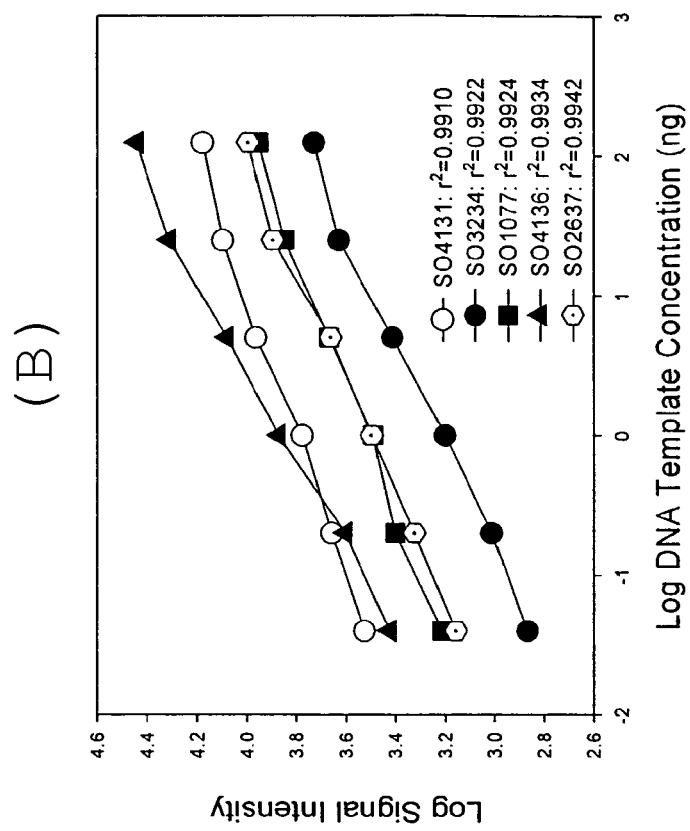
Figure 5:
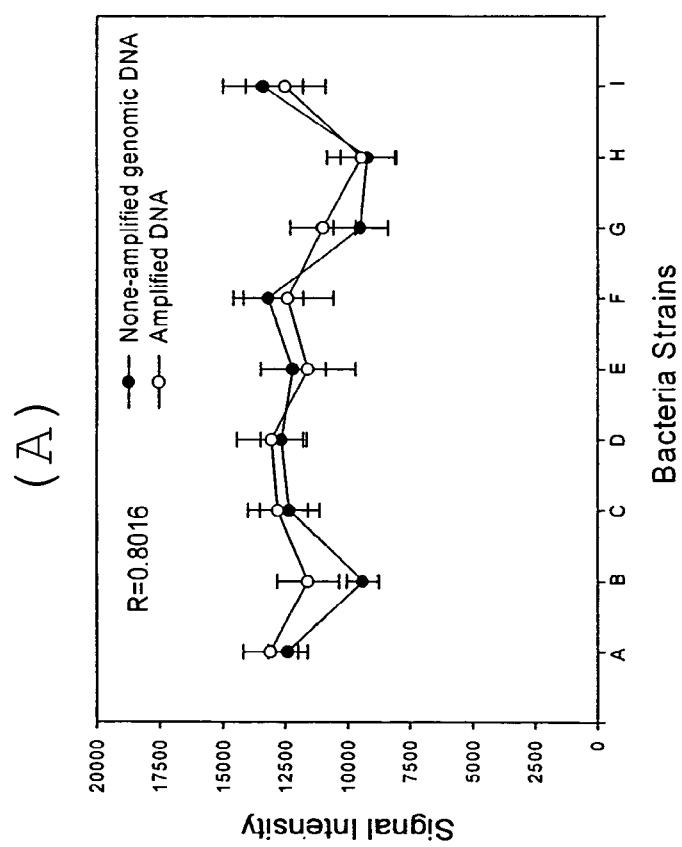

Representational detection determined using community genome arrays: Although individual genes can not be equally amplified, it is possible that the overall amplification of a whole genome could be equal. To test this hypothesis, genomic DNAs from 9 different species were mixed in equal quantity (1 pg each) and amplified with Phi29 for 2 hours in triplicate. The amplified genomic DNAs were labeled with Cy5 and then 1.111 μg of the amplified genomic DNA was co-hybridized with 1.111 μg non-amplified genomic DNA using community genome arrays containing the whole genomic DNA as probe (Wu et al. 2004). For individual genomes, no significant differences in the hybridization signal intensity (P=0.05) were observed between the amplified DNA and non-amplified genomic DNA (FIG. 5A). Significant correlations of the average signal intensity between the amplified DNA and the non-amplified DNA were obtained among the 9 microbial genomes. These results indicate that amplification at the whole genome level is representative.

Quantitation of whole community genome amplification-assisted ORF microarray-based hybridization: The assessment of microbial community composition and structure requires the quantification of individual target genes/populations. To determine whether the isothermal DNA polymerase-assisted microarray hybridization is quantitative, genomic DNA from S. oneidensis MR-1 were diluted in 5 fold series resulting in concentrations ranging from 0.04 to 125 ng (125, 25, 5, 1, 0.2, and 0.04 ng). To ensure that the amplified DNAs were sampled at exponential phase, the diluted DNAs were amplified for 2 hours in triplicate. An average of approximately 0.1, 0.3, 1.3, 2.9, 5.1, 8.5, and 12.2 µg DNAs were obtained for each dilution, respectively. All of the amplified DNAs were labeled with Cy5 and co-hybridized with 2, Cy3-labeled non-amplified genomic DNAs. Dye switching experiments were also conducted. Poor spots and outliers were removed as described above and altogether 4173 genes remained. The average signal intensities of individual genes at each dilution were obtained and linear regression models were fitted between signal intensities and DNA concentrations. About 80% of the 4173 effective genes showed significant linear relationships of the signal intensities to DNA concentrations ($r^2$=0.65-0.99; P=0.05), while 86% of the genes showed significant linear relationships at P=0.1 ($r^2$=0.53-0.99). The linear relationships for some representative genes are shown in FIG. 5B. These results suggest that the isothermal DNA polymerase-assisted ORF microarray hybridizations were quantitative for the majority of the genes.

Quantitation of whole community genome amplification-assisted Community Genome Array hybridization: To determine whether the isothermal DNA polymerase-assisted microarray hybridization is quantitative for target organisms in the presence of other non-target DNAS, the quantitative relationships between signal intensity and DNA concentrations were further examined using community genome arrays containing the entire genomic DNA from 5 bacterial species representing different genera and species. The DNAs from these species were mixed unequally (0.1, 1, 10, 100, and 1,000 ng) and amplified in triplicate for 2 hours. Then, the same amount of the amplified DNA as was used for the original template DNA (1111.1 ng in total) was labeled with Cy3 or Cy5 and co-hybridized with the same amount of Cy5- or Cy3-labeled nonamplified DNA mixtures.

Figure 6:
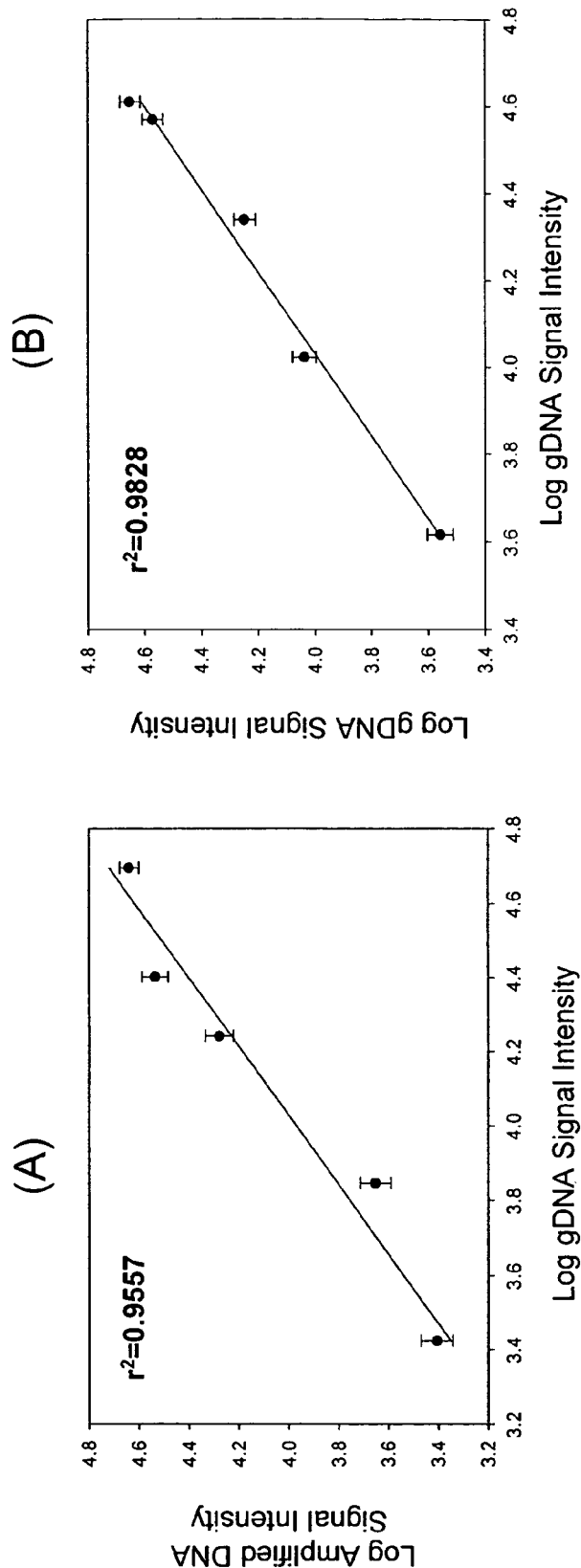
FIG. 6 shows representative amplification with unequal mixed DNA from 5 species (*Paracoccus denitrificans, Thauera aromatica, Rhodopseudomonas palustris, Shewanella oneidensis* MR-1, and *Chrobactrum anthropi*). The DNAs from these species were mixed unequally, amplified, then equal amounts of the amplified DNA were labeled with Cy3 or Cy5 and co-hybridized with Cy5- or Cy3-labeled nonamplified DNA mixtures.

A very strong linear relationship ($r^2$=0.91) of the signal intensity between the amplified and non-amplified DNAs ranging from 0.1 to 1000 ng was obtained (FIG. 6A). This was similar to the relationship between the signal intensities of the self genomic DNA and genomic DNA hybridization (FIG. 6B). These results indicated that the overall genomic DNA amplification is representative for mixed DNA templates.

Figure 7:
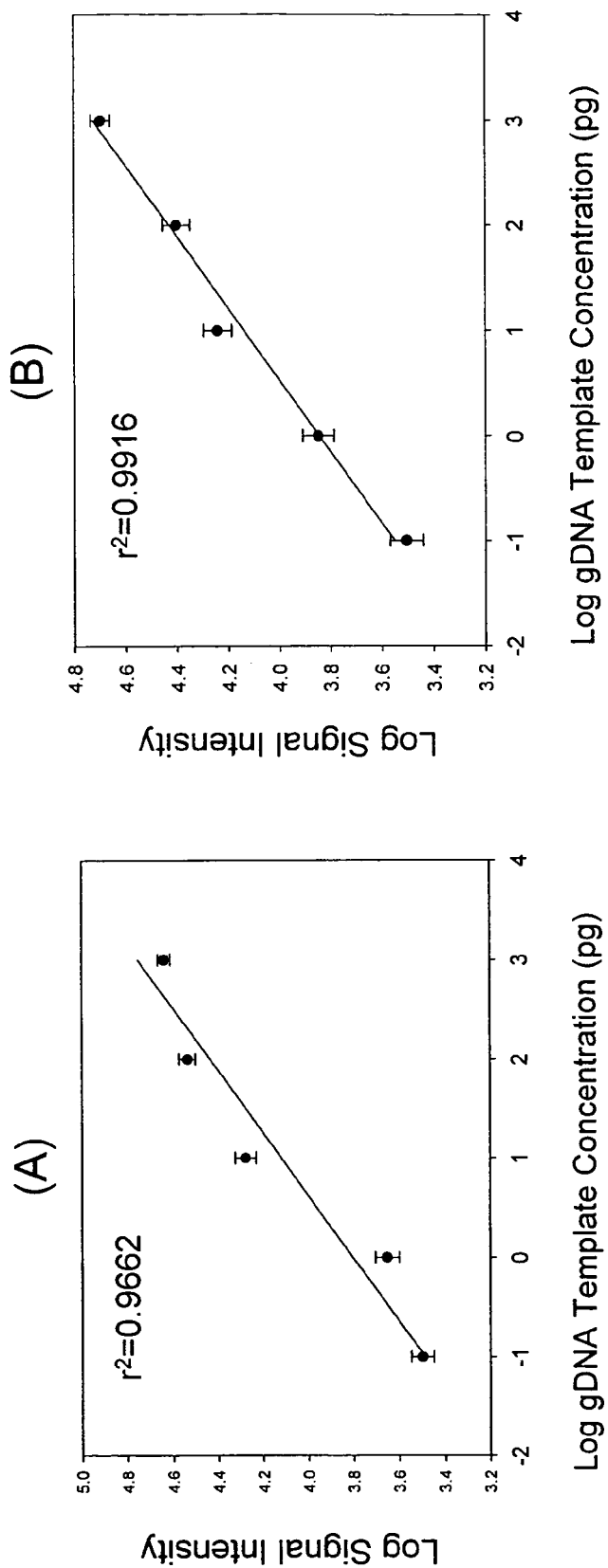
FIG. 7 shows quantitative detection with unequally mixed DNA from 5 species (*Paracoccus denitrificans, Thauera aromatica, Rhodopseudomonas palustris, Shewanella oneidensis* MR-1, and *Chrobactrum anthropi*). The DNAs from these species were mixed unequally, amplified, then equal amounts of the amplified DNA were labeled with Cy3 or Cy5 and co-hybridized with Cy5- or Cy3-labeled nonamplified DNA mixtures.

The quantitative relationships between the hybridization signal intensity and the concentration of template genomic DNA used for amplification were further analyzed. Similar to the results above (FIG. 6), a very strong linear relationship ($r^2$=0.93) between signal intensity and DNA concentrations ranging from 0.1 to 1000 ng was obtained (FIG. 7A), which was similar to the relationship between signal intensities of the self genomic DNA-genomic DNA hybridization (FIG. 7B). These results suggest that the overall genomic DNA amplification could also be quantitative for mixed DNA templates.

Representative and quantitative detection of environmental samples: To determine whether representative and quantitative amplification and detection can be obtained with real environmental samples, a uranium-contaminated groundwater sample (FW029) from the Field Research Center (FRC) of the U.S. Department of Energy's Natural and Accelerated Bioremediation Research (NABIR) Program was used. The sample was taken from a well stimulated with ethanol. The community DNA was isolated and diluted (500, 250, 100, 50, 10, 1, 0.1 and 0.01 ng). The diluted DNAs were amplified for 2 hours and all of the amplified DNA were labeled with Cy5 and co-hybridized together with 2 µg non-amplified community DNA using a 50-mer-based oligonucleotide microarray, which contained about 2,000 probes from the genes involved in carbon cycling, nitrogen cycling, sulfate reduction, contaminant degradation and metal resistance. A significant number of the probes involved in nitrification, denitrification and sulfate-reduction were derived from FRC samples. Altogether 61 genes were detected in the non-amplified DNA samples (Table 6). More than 90% of these genes were detected when total template DNA concentrations were greater than 1 ng and more than 50% of the genes were detected at template DNA concentrations as low as 10 pg (Table 6). The average representational bias was slightly higher at the DNA concentration of 10 ng (0.0768) than at 1 ng (0.0987). The average representational biases at 100 and 10 pg were 6 times higher than those at 10 ng. However, the representational bias was also relatively higher at the template concentrations of greater than 50 ng (Table 6). In addition, less than 5% of the genes showed 2 fold differences for the amplified DNA samples when the DNA template concentration was greater than 1 ng (Table 6). These results indicate that the whole community amplification is representative when using real environmental samples.

TABLE 6

Representative and quantitative detection of environmental samples.

| Parameter | DNA template (ng) | | | | | | | | control |
| --- | --- | --- | --- | --- | --- | --- | --- | --- | --- |
| | 500 | 250 | 100 | 50 | 10 | 1 | 0.1 | 0.01 | |
| Genes present | 59 | 60 | 60 | 60 | 59 | 57 | 40 | 31 | 61 |
| Gene coverage (%) | 96.7 | 98.3 | 98.3 | 98.3 | 96.7 | 93.4 | 65.5 | 50.8 | |
| Representational bias ($D^{total}$) | 0.164 | 0.127 | 0.150 | 0.125 | 0.076 | 0.098 | 0.465 | 0.452 | |
| % of >2 folds | 3.4 | 8.3 | 18.3 | 6.7 | 1.7 | 5.3 | 92.5 | 58.1 | |
| % of >2 folds | 3.3 | 3.3 | 5.0 | 3.3 | 1.7 | 0 | 80.0 | 48.4 | |
| % of >3 folds | 3.4 | 1.7 | 1.7 | 1.7 | 0 | 0 | 42.5 | 29.0 | |
| % of >4 folds | 3.4 | 1.7 | 1.7 | 1.7 | 0 | 0 | 17.5 | 19.4 | |

Figure 8:
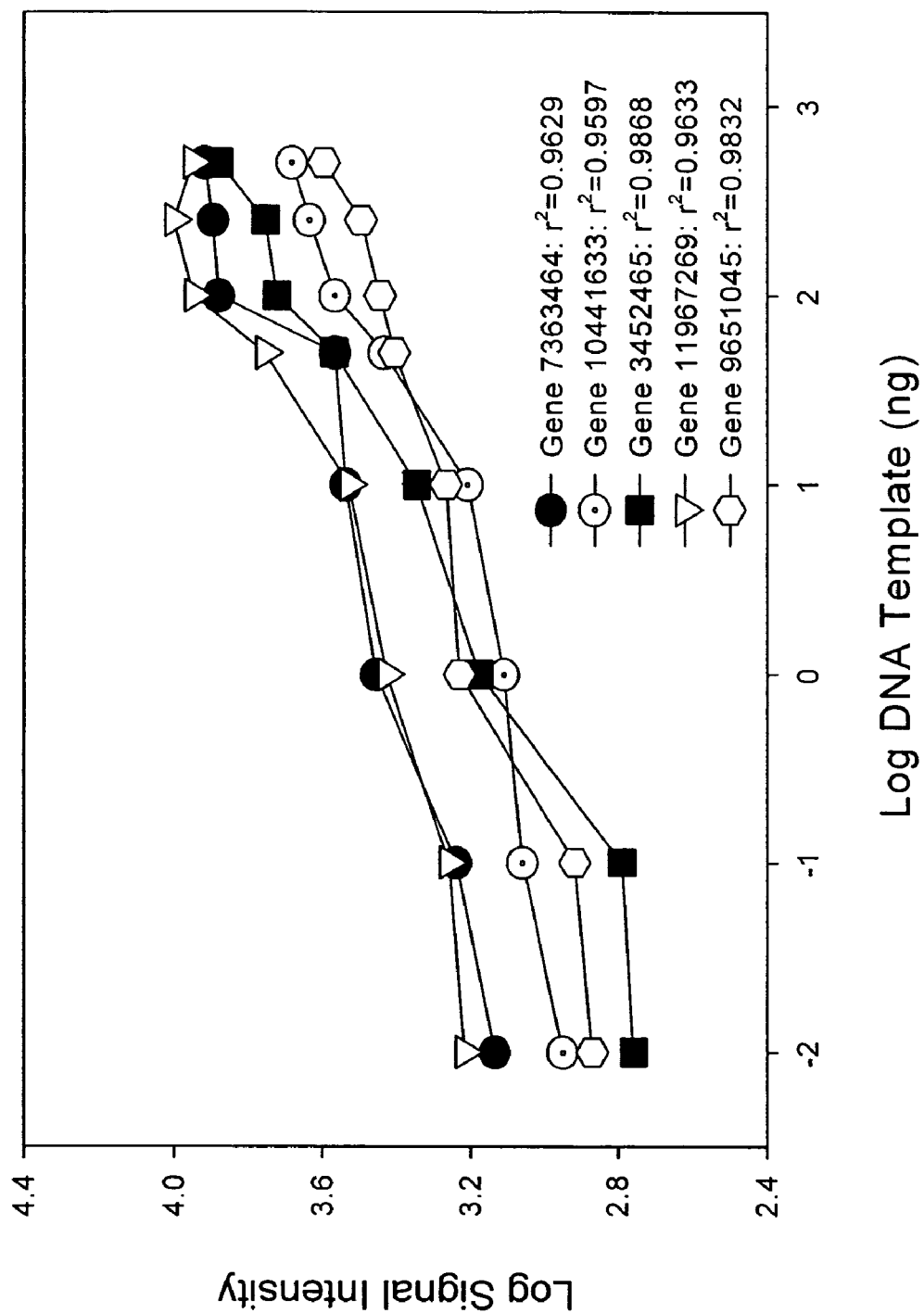
FIG. 8 shows quantitative amplification and detection of representative genes from groundwater sample FW29. The genes are identified by the Gene ID numbers and they can be found in the GenBank of NCBI.

The quantitative relationships between the hybridization signal intensity and template genomic DNA used for amplification were further analyzed. All of the genes showed significant linear relationships between signal intensity and DNA concentrations ranging from 0.01 to 250 ng (n=6-8; $r^2$=0.30-0.96). The linear relationships for some representative genes are shown in FIG. 8. These results suggest that the isothermal DNA polymerase-assisted 50-mer oligonucleotide microarray hybridizations are quantitative within a wide of range of DNA concentrations for real environmental samples.

Application of whole community genome-assisted microarray hybridization for profiling microbial communities in environmental samples: Microarrays could potentially be used as a generic profiling tool that would reveal differences among various microbial communities. We have constructed microarrays containing more than 2,000 oligonucleotide probes from genes involved in carbon cycling, nitrogen cycling, sulfate reduction, contaminant degradation and metal resistance that are used for monitoring microbial community dynamics in FRC groundwaters. However, due to low biomass, we could not obtain sufficient DNA for microarray hybridization. In this study we therefore explored the power of the developed isothermal DNA polymerase-assisted microarray hybridization to understand how contaminants impact microbial community structure and how a microbial community adapts to environmental conditions. Six wells at the NABIR FRC with different levels of contaminants were selected and 2 L of groundwater were sampled from each well. DNAs were isolated and 5% of the isolated DNA was used for amplification for 2 hours. All of the amplified DNAs were labeled with Cy5. As a reference control, the community genomic DNA from well FW29 was amplified and labeled with Cy3. The Cy3 and Cy5-labeled community DNAs were mixed and hybridized to the 50-mer oligonucleotide in triplicate. All spots with signal-to-noise ratio (SNR)>3 were considered as positive signals. Very good hybridization was obtained for all of the amplified samples. Overall, the numbers of arrayed probes with statistically significant positive signals were 311 in the background well (FW300), 136 in FW010, 207 in FWO21, 195 in FW024, 228 in FW003 and 139 in TPB16. No hybridization signal was observed for negative human control genes. As expected, the uncontaminated background sample had the highest diversity (FW300) while the highly contaminated sample (FW010) had the lowest diversity. These results indicate that the whole community genome amplification-assisted microarray-based hybridization is useful for characterizing challenging samples which could not be characterized using the conventional microarray-based technologies.

REFERENCES

Andras S C, Power J B, Cocking E C, Davey M R. Strategies for signal amplification in nucleic acid detection. *Mo. Biotechno.* 2001, 19:29-44.

Cho, J. C. and Tiedje, J. M. Quantitative detection of microbial genes by using DNA micrarrays. *Appl. Environ. Microbiol.* 2002, 68, 1425-1430.

Dean F B, Hosono S, Fang L H, Wu X H, Faruqi A F, Bray-Ward P, Sun Z Y, Zong Q L, Du Y F, Du J, Driscoll M, Song W M, Kingsmore S F, Egholm M, Lasken R S. Comprehensive human genome amplification using multiple displacement amplification. *Proc Natl Acad Sci* 2002, 99:5261-5266.

DeRisi J L, Iyer V R, Brown P O. Exploring the metabolic and genetic control of gene expression on a genomic scale. *Science* 1997, 278:680-686.

Eisen, M. B., Spellman, P. T., Brown, P. O., and Botstein, D. Cluster analysis and display of genome-wide expression patterns. Proc. Natl. Acad. Sci. 1998, 95, 14863-14868.

Gao, H., Y. Wang, X. Liu, T. Yan, L. Wu, E. Alm, A. Arkin, D. K. Thompson, and J.-Z. Zhou. Global Transcriptome Analysis of the Heat Shock Response of *Shewanella oneidensis*. *J. Bacteriol.* 2004.

Guschin D G, Yershov A, Zaslavsky A, Gemmell V, Shick D, Proudnikov D, Arenkov P, Mirzabekov A. Manual manufacturing of oligonucleotide, DNA, and protein microchips. *Anal Biochem* 1997a, 250:203-211.

Guschin D Y, Mobarry B K, Proudnikov D, Stahl D A, Rittmann B E, Mirzabekov A D. Oligonucleotide microchips as genosensors for determinative and environmental studies in microbiology. *Appl Environ Microbiol* 1997b, 63:2397-2402.

Khodursky A B, Peter B J, Cozzarelli N R, Botstein D, Brown P O, Yanofsky C. DNA microarray analysis of gene expression in response to physiological and genetic changes that affect tryptophan metabolism in *Escherichia coli*. *Proc Natl Acad Sci USA* 2000, 97:12170-12175.

Lage J M, Leamon J H, Pejovic T, Hamann S, Lacey M, Dillon D, Segraves R, Vossbrinck B, Gonzalez A, Pinkel D, Albertson D G, Costa J, Lizardi P M. Whole genome analysis of genetic alterations in small DNA samples using hyperbranched strand displacement amplification and array-CGH. *Genome Research* 2003, 13: 294-307.

Liu Y, Zhou J, Omelchenko M, Beliaev A, Venkateswaran A, Stair J, Wu L, Thompson D K, Xu D, Rogozin I B et al. Transcriptome dynamics of *Deinococcus radiodurans* recovering from ionizing radiation. *Proc Natl Acad Sci USA* 2003, 100: 4191-4196.

Lockhart D J, Dong H, Byrne M C, Follettie M T, Gallo M V, Chee M S, Mittmann M W, Wang C, Kobayashi M, Horton H, Brown E L. Expression monitoring by hybridization to high-density oligonucleotide arrays. *Nat Biotechnol* 1996, 14:1675-1680.

Loy A, Lahner A, Lee N, Adamczyk J, Meier H, Ernst J, Schleifer K H, Wagner M. Oligonucleotide microarray for 16S rRNA gene-based detection of all recognized lineages of sulfate-reducing prokaryotes in the environment. *Appl Environ Microbiol* 2002, 68:5064-5081.

Nallur G C, Luo H, Fang L H, Cooley S, Dave V, Lambert J, Kukanskis K, Kingsmore S, Lasken R, Schweitzer B. Signal amplification by rolling circle amplification on DNA microarrays. *Nucleic Acid Res* 2001, 29:E118.

Rhee, S. K., Liu, X. D., Wu, L. Y., Chong, S. C., Wan, X. F., and Zhou, J. Z. Detection of genes involved in biodegradation and biotransformation in microbial communities by using 50-mer oligonucleotide microarrays. Applied and Environmental Microbiology 2004, 70: 4303-4317.

Richmond C S, Glasner J D, Mau R, Jin H, Blattner F R. Genome-wide expression profiling in *Escherichia coli* K-12. *Nucleic Acids Res* 1999, 27:3821-3835.

Rudi K, Skulberg O M, Skulberg R, Jakobsen K S. Application of sequence-specific labeled 16S rRNA gene oligonucleotide probes for genetic profiling of cyanbacterial abundance and diversity by array hybridization. *Appl Environ Microbiol* 2000, 66:4004-4011.

Sambrook, J., Fritsch, E. F., Maniatis, T. Molecular Cloning. A laboratory manual. Second Edition. Cold Spring Harbor, N.Y.: Cold Spring Harbor laboratory Press, 1989.

Schena M, Shalon D, Heller R, Chai A, Brown P O, Davis R W. Parallel human genome analysis: microarray-based expression monitoring of 1000 genes. *Proc Natl Acad Sci USA* 1996, 93:10614-10619.

Schweitzer B, Roberts S, Grimwade B, Shao W P, Wang M J, Fu Q, Shu Q P, Laroche I, Zhou Z M, Tchernev V T, Christiansen J, Velleca M, Kingsmore S F. Multiplexed protein profiling on microarrays by rolling-circle amplification. *Nat Biotech* 2002, 20:359-365.

Shalon D, Smith S J, Brown P O. A DNA microarray system for analyzing complex DNA samples using two-color fluorescent probe hybridization. *Genome Res* 1996, 6:639-645.

Small J, Call D R, Brockman F J, Straub T M, Chandler D P. Direct detection of 16S rRNA in soil extracts by using oligonucleotide microarrays. *Appl Environ Microbiol* 2001, 67:4708-4716.

Spellman P T, Sherlock G, Zhang M Q, Iyer V R, Anders K, Eisen M B, Brown P O, Botstein D, Futcher B. Comprehensive identification of cell cycle-regulated genes of the yeast *Saccharomyces cerevisiae* by microarray hybridization. *Mol Biol Cell* 1998, 9:3273-3297.

Straub T M, Daly D S, Wunshel S, Rochelle P A, DeLeon R, Chandler D P. Genotyping *Cryptosporidium parvum* with an hsp70 single-nucleotide polymorphism microarray. *Appl Environ Microbiol* 2002, 68:1817-1826.

Tao H, Bausch C, Richmond C, Blattner F R, Conway T. Functional genomics: expression analysis of *Escherichia coli* growing on minimal and rich media. *J Bacteriol* 1999, 181:6425-6440.

Taroncher-Oldenburg G, Griner E M, Francis C A, Ward B B. Oligonucleotide microarray for the study of functional gene diversity in the nitrogen cycle in the environment. *Appl Environ Microbiol* 2003, 69:1159-1171.

Thompson D K, Beliaev A S, Giometti C S, Tollaksen S L, Khare T, Lies D P, Nealson K H, Lim H, Yates J III, Brandt C C et al. Transcriptional and proteomic analysis of a ferric uptake regulator (Fur) mutant of *Shewanella oneidensis*: possible involvement of Fur in energy metabolism, transcriptional regulation, and oxidative stress. *Appl Environ Microbiol* 2002, 68:881-892.

Urakawa H, Noble P A, El Fantroussi S, Kelly J J, Stahl D A. Single-base-pair discrimination of terminal mismatches by using oligonucleotide microarrays and neural network analyses. *Appl Environ Microbiol* 2002, 68:235-244.

Verdick, D., Handran, S., and Pickett. S. Key considerations for accurate microarray scanning and image analysis. In G. Kamberova (ed.), DNA image analysis: Nuts and Bolts, DNA Press LLC, Salem, Mass. Pp 83-98 (2002).

Wei Y, Lee J M, Richmond C, Blattner F R, Rafalski J A, LaRossa R A. High-density microarray-mediated gene expression profiling of *Escherichia coli*. *J Bacteriol* 2001, 183:545-556.

Wilson K H, Wilson W J, Radosevich J L, DeSantis T Z, Viswanathan V S, Kuczmarski T A, Andersen G L. High-density microarray of small-subunit ribosomal DNA probes. *Appl Environ Microbiol* 2002, 68:2535-2541.

Wodicka L, Dong H, Mittman M, Ho M H, Lockhart D J. Genome-wide expression monitoring in *Saccharomyces cerevisiae*. *Nat Biotechnol* 1997, 15:1359-1367.

Wodicka L, Dong H, Mittmann M, Ho M H, Lockhart D J. Genome-wide expression monitoring in *Saccharomyces cerevisiae*. *Nat Biotechnol* 1997, 15:1359-1367.

Wu H C, Shieh J, Wright D J, Azarani A. DNA sequencing using rolling circle amplification and precision glass syringes in a high-throughput liquid handling system. *Biotechniques* 2003a, 34:204-207.

Wu L Y, Thompson D K, Xueduan L, Bagwell C E, Fields M W, Tiedje J M, Zhou J. Development and evaluation of microarray-based whole-genome hybridization for detection of microorganisms within the context of environmental applications. *Environmental Science and Technology* 2004, in press.

Wu L Y, Thompson D, Li G S, Hurt R, Huang H, Tiedje J M, Zhou J. Development and evaluation of functional gene arrays for detection of selected genes in the environment. *Appl Environ Microbiol* 2001, 67: 5780-5790.

Ye R W, Tao W, Bedzyk L, Young T, Chen M, Li L. Global gene expression profiles of *Bacillus subtilis* grown under anaerobic conditions. *J Bacteriol* 2000, 182:4458-4465.

Zhou, J. Z., Bruns, M. A., and Tiedje, J. M. ( ) DNA recovery from soils of diverse composition. *Applied and Environmental Microbiology* 1996, 62: 316-322.

Zhou, J. Z., Palumbo, A. V., and Tiedje, J. M. Sensitive detection of a novel class of toluene-degrading denitrifiers, *Azoarcus tolulyticus*, with small-subunit rRNA primers and probes. *Applied and Environmental Microbiology* 1997, 63: 2384-2390.

Zhou, J, Thompson D K. Challenges in applying microarrays to environmental studies. *Curr Opin Biotechnol* 2002, 13:204-207.

Zhou, J. Microarrays for bacterial detection and microbial community analysis. *Curr Opinion Microbiol* 2003, 6:288-294.

We claim:

1. A method for quantifying microbial genes, species, or strains in a sample, the method comprising the steps of:
   providing an unpurified environmental sample comprising at least two different microbial species or strains;
   providing a polynucleotide microarray that can differentiate said at least two different microbial species or strains or at least two different genes from the different microbial species or strains;
   randomly, representatively and quantitatively amplifying genomic DNA in the sample with a buffer that comprises spermidine and a single strand binding protein to form a polynucleotide preparation for hybridization;
   hybridizing the polynucleotide preparation to the microarray; and
   quantitatively measuring hybridization signals on the microarray wherein a signal intensity difference between two different microbial genes, species, or strains will be quantitatively observed if the total amount of DNA in the sample of a less abundant microbial gene, species, or strain in the sample is 20% or less by weight of the total amount of DNA in the sample of a more abundant microbial gene, species, or strain in the sample.

2. The method of claim 1, wherein a signal intensity difference between two different microbial genes, species, or strains of interest will be quantitatively observed if the total amount of DNA of the less abundant microbial gene, species, or strain is 30% or less by weight of the total amount of DNA of the more abundant microbial gene, species, or strain.

3. The method of claim 1, wherein a signal intensity difference between two different microbial genes, species, or strains of interest will be quantitatively observed if the total amount of DNA of the less abundant microbial gene, species, or strain is 50% or less by weight of the total amount of DNA of the more abundant microbial gene, species, or strain.

4. The method of claim 1, wherein a signal intensity difference between two different microbial genes, species, or strains of interest will be quantitatively observed if the total amount of DNA of the less abundant microbial gene, species, or strain is 60% or less by weight of the total amount of DNA of the more abundant microbial gene, species, or strain.

5. The method of claim 1, wherein the total amount of DNA of the less abundant microbial gene, species, or strain is from about 100 fg to about 1 ng.

6. The method of claim 1, wherein the total amount of DNA of the less abundant microbial gene, species, or strain is from about 100 fg to about 100 pg.

7. The method of claim 1, wherein the total amount of DNA of the less abundant microbial gene, species, or strain is from about 100 fg to about 10 pg.

8. The method of claim 1, wherein the microarray is a DNA microarray.

9. The method of claim 1, wherein the microarray has at least two detection elements wherein each detection element comprises one or more nucleotide sequences specific for one gene, species, or strain of the microorganisms in the sample but not other genes, species, or strains in the same sample.

10. The method of claim 1, wherein the microarray is selected from a whole genome microarray, a whole genome open reading frame microarray, and an oligonucleotide-based microarray.

11. The method of claim 1, wherein the random amplification is conducted with an isothermal DNA polymerase.

12. The method of claim 11, wherein the isothermal DNA polymerase is selected from phi29 and Bst.

13. A method for quantifying microbial genes, species, or strains in a sample, the method comprising the steps of:
provising an unpurified environmental sample comprising at least two different microbial species or strains;
providing a polynucleotide microarray that can differentiate said at least two different microbial species or strains or at least two different genes from the different microbial species or strains;
randomly, representatively and quantitatively amplifying genomic DNA in the sample with a buffer that comprises spermidine and *E. coli* wild type single strand binding protein to form a polynucleotide preparation for hybridization;
hybridizing the polynucleotide preparation to the microarray; and
quantitatively measuring hybridization signals on the microarray wherein a signal intensity difference between two different microbial genes, species, or strains will be quantitatively observed if the total amount of DNA in the sample of a less abundant microbial gene, species, or strain in the sample is 20% or less by weight of the total amount of DNA in the sample of a more abundant microbial gene, species, or strain in the sample.

14. The method of claim 1 further comprising the step of labeling polynucleotides in the polynucleotide preparation.

15. The method of claim 14, wherein the labeling step is conducted with a buffer that comprises spermidine, a RecA protein, or both.

16. The method of claim 15, wherein the RecA protein is *E. coli* wild type RecA protein.

17. The method of claim 1, wherein the hybridization step is conducted with a buffer that comprises spermidine, RecA protein, or both.

18. The method of claim 17, wherein the RecA protein is *E. coli* wild type RecA protein.

19. The method of claim 1, wherein the sample contains at least 3 microbial species or strains.

20. The method of claim 1, wherein the sample contains at least 10 microbial species or strains.

21. The method of claim 1, wherein the microbial genes, species, or strains are selected from viruses, bacteria, yeasts, fungi, and algae.

22. The method of claim 1, wherein the microbial genes, species, or strains are bacterial genes, species or strains.

* * * * *